US012797193B2

(12) United States Patent
Song et al.

(10) Patent No.: US 12,797,193 B2
(45) Date of Patent: Nov. 17, 2026

(54) NINE AXIS INERTIAL MEASUREMENT UNIT FOR SCORING COMBATIVE SPORTS

(71) Applicants: Jin Song, Morgan Hill, CA (US); Tyler Delarosa, New York, NY (US)

(72) Inventors: Jin Song, Morgan Hill, CA (US); Tyler Delarosa, New York, NY (US)

( * ) Notice: Subject to any disclaimer, the term of this patent is extended or adjusted under 35 U.S.C. 154(b) by 58 days.

(21) Appl. No.: 18/831,290

(22) Filed: Oct. 21, 2024

(65) Prior Publication Data

US 2025/0248816 A1 Aug. 7, 2025

Related U.S. Application Data

(63) Continuation of application No. 18/445,582, filed on Oct. 31, 2023, now Pat. No. 12,150,854, which is a continuation-in-part of application No. 17/087,006, filed on Nov. 2, 2020, now Pat. No. 11,844,989, which is a continuation-in-part of application No. 16/708,114, filed on Dec. 9, 2019, now Pat. No. 11,351,437, which is a continuation-in-part of application No. 14/280,370, filed on May 16, 2014, now Pat. No. 10,500,471.

(60) Provisional application No. 61/824,946, filed on May 17, 2013.

(51) Int. Cl.

| | |
|---|---|
| ***A61F 2/24*** | (2006.01) |
| ***A61B 17/00*** | (2006.01) |
| ***A61B 17/064*** | (2006.01) |
| ***A61B 17/068*** | (2006.01) |

(52) U.S. Cl.

CPC .......... *A61F 2/2442* (2013.01); *A61B 17/068* (2013.01); *A61B 2017/00243* (2013.01); *A61B 2017/00331* (2013.01); *A61B 2017/00349* (2013.01); *A61B 2017/00783* (2013.01); *A61B 2017/0649* (2013.01); *A61F 2/2412* (2013.01); *A61F 2002/249* (2013.01); *A61F 2230/0091* (2013.01)

(58) Field of Classification Search

None

See application file for complete search history.

(56) References Cited

U.S. PATENT DOCUMENTS

| | | | | |
|---|---|---|---|---|
| 2014/0150521 A1* | 6/2014 | Jacobson | G01C 25/00 | 73/1.38 |
| 2014/0228985 A1* | 8/2014 | Elliott | A61B 5/11 | 700/91 |
| 2014/0343701 A1* | 11/2014 | Song | A63B 71/10 | 700/92 |
| 2019/0347922 A1* | 11/2019 | Burton | G01P 15/0891 | |
| 2021/0172975 A1* | 6/2021 | Song | A63B 71/0605 | |

* cited by examiner

*Primary Examiner* — Ronald Laneau

(74) *Attorney, Agent, or Firm* — Dan Delarosa

(57) ABSTRACT

A motion tracking system for validating an athlete's movement technique to determine an accurate competitive scoring with a nine-axis inertial measurement unit comprises: a three axis accelerometer, a three axis-gyroscope, a three axis-magnetometer and at least one sensor.

20 Claims, 24 Drawing Sheets

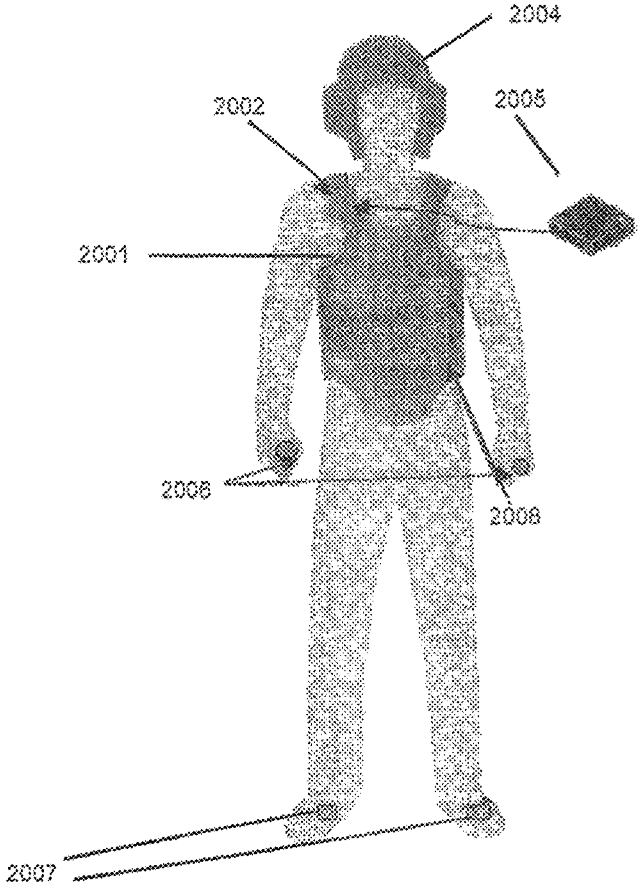
Figrue 18
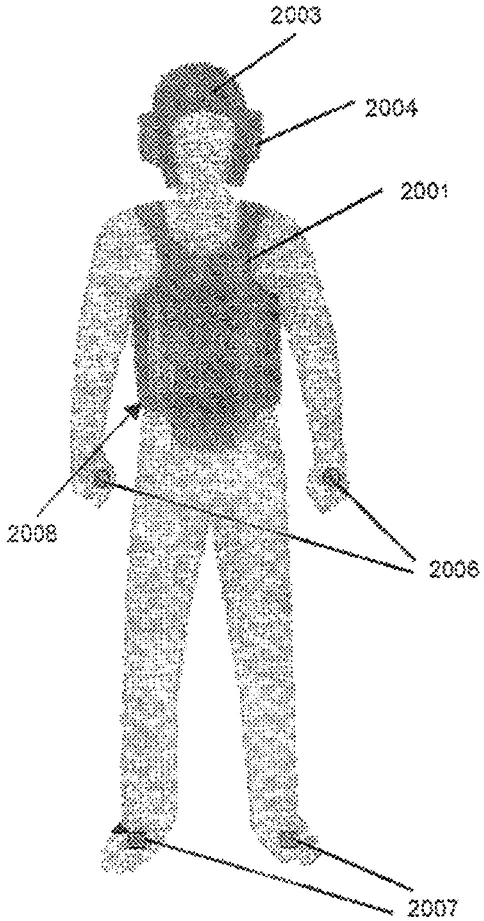
Figure 19

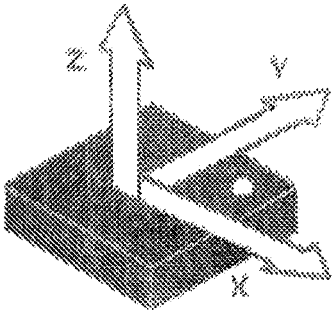
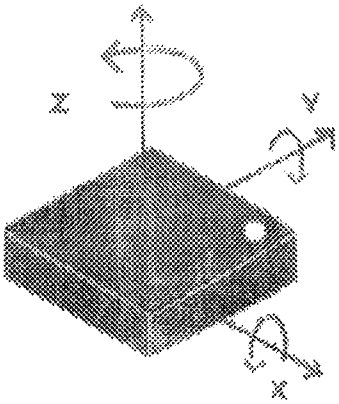
Figure 23

NINE AXIS INERTIAL MEASUREMENT UNIT FOR SCORING COMBATIVE SPORTS

RELATED APPLICATIONS

This application is a continuation of U.S. patent application Ser. No. 18/445,582 filed on Oct. 31, 2023 entitled "Martial Arts Glove With Electronic Scoring System", which is a continuation-in-part and claims priority to the U.S. patent application Ser. No. 17/087,006 filed on Nov. 2, 2020 entitled "Impact Sensor Embedded Protector with Nine-Axis Inertial Measurement Unit for Scoring Combative Sports", which is a continuation-in-part and claims priority to U.S. patent application Ser. No. 16/708,114 filed on Dec. 9, 2019 entitled "Impedance Based Determination and Scoring" which claims priority to is a continuation-in-part of U.S. Pat. No. 10,500,471 which was filed as U.S. application Ser. No. 14/280,370 filed on May 16, 2014 entitled "Impedance-Based Impact Determination and Scoring" which claims priority to the U.S. Provisional No. 61/824,946 filed May 17, 2013, entitled "Impedance-Based Impact Determination and Scoring".

BACKGROUND OF THE INVENTION

In the field of competitive combative sports, evaluating and scoring techniques is a nuanced and error prone process. Many techniques occur at speeds that make visual identification challenging, whether due to poor visibility or inadequate judge reflex. Rules which specify minimum scoring impact levels add an extra layer of technical complexity, as impacts cannot be accurately gauged by visual confirmation alone. The Olympic sport of Taekwondo (a full contact combative sport) first featured a semi-automated, electronic scoring system at the 2012 Olympic Games in London to address repeated controversies stemming from judging error. However, within a few years, athletes have acclimated to the impact sensor characteristics. Techniques and fighting styles have changed drastically, prompting the World Taekwondo Federation to implement ever changing rules to support a more dynamic and visually appealing sport.

The proposed invention is a further improvement of a prior patent (Pat. No. 7,891,231 B2) which detects and measures the magnitude of valid contact to the scoring areas. This patent implements an additional sensor type: a nine-axis inertial measurement unit (IMU). The 9-axis IMU includes a 3-axis magnetometer, a 3-axis accelerometer and 3-axis gyroscope. The 3-axis magnetometer measures direction relative to the earth magnetic field, the 3-axis accelerometer measures the acceleration in 3 dimensional space, while the 3-axis gyroscope measures the angular velocity about the axis. With these sensors and math to estimate the motion, one can track the rotational movement of the players. The addition of a 9-axis IMU allows the system to monitor the player's rotation, and thus paired with proper software analysis, identify rotating or non-rotating martial arts techniques. This extra layer of identification allows for the application of additional scoring rules tailored to specific technique profiles.

The IMU is used in navigation of drones, Unmanned Aerial Vehicles (UAV), and robotics. One of the main elements in the IMU is 3-axis magnetometer, 3-axis accelerometer and 3-axis Gyros. In UAV, these sensors are used to compute the Heading, Roll, and Pitch angle orientations referenced to the earth gravity and magnetic field. The magnetometer measures the earth magnetic field in three dimensions, the accelerometers measure the acceleration in three dimensions while Gyros measures rotation of an object about the axis of the dimensions. The accelerometer is used to compute the orientation of the object referenced to earth gravity. By mathematically combining the sensors, Heading, Roll, Pitch orientation of an object referenced to the earth gravity and magnetic field is derived to aid in navigation. A full description of a method used to compute orientation for navigation is readily available in the market.

An area of ongoing research and development is systems and methods to provide for accurate scoring of athletic events. More recently instant replay has been instituted in various sports to allow officials to review plays and calls made by the officials. However, in many sports, human scoring and officiating still produces a controversial margin of error. With athletes pushing the envelope of human performance, it becomes more difficult for humans to officiate and score athletic events. There therefore exists the need for systems and methods that further remove officiating and scoring duties away from humans in athletic events.

The foregoing examples of the related art and limitations related therewith are intended to be illustrative and not exclusive. Other limitations of the relevant art will become apparent to those of skill in the art upon reading the specification and studying of the drawings.

SUMMARY OF THE INVENTION

The following implementations and aspects thereof are described and illustrated in conjunction with systems, tools, and methods that are meant to be exemplary and illustrative, not necessarily limiting in scope. In various implementations one or more of the above-described problems have been addressed, while other implementations are directed to other improvements. Various implementations include systems and methods for scoring an athletic event based on changes in impedance in impedance-based impact measuring sporting equipment as a result of impacts delivered during the athletic event. In various implementations, a conductive material of a plurality of separate conductive materials is coupled to a first participant, the conductive material configured to move when the first participant delivers an impact to a second participant. Further, in various implementations, an impedance-based impact sensing mechanism including an impedance changing mechanism that changes impedance as the conductive material is moved towards and away from the impedance changing mechanism as the first participant delivers the impact. In various implementations, an impedance-based impact measuring scoring system determines that the impact occurred based on a change in impedance in the impedance changing mechanism. These and other advantages will become apparent to those skilled in the relevant art upon a reading of the following descriptions and a study of the several examples of the drawings. In one embodiment, the present invention relates to a motion tracking device for tracking athletic movement for accurate competitive scoring, the device comprising a nine-axis inertial measurement unit comprising a three axis magnetometer, a three-axis accelerometer and a three-axis gyroscope; and at least one other type of sensor. In another embodiment a device wherein the sensor is selected from a group consisting essentially of impact sensor, proximity sensor, magnetic proximity sensor, metal detector proximity sensor, 3 axis magnetic compass and combinations thereof. In yet another an embodiment, wherein the three-axis accelerometer measures directional acceleration of an athlete's movement.

In a further embodiment, the three axis-gyroscope measures rotational motion of an athlete's movement. In yet a further embodiment, wherein said nine-axis inertial measurement unit is located in an article selected from a group comprising an athlete's uniform, sporting equipment, protective equipment, clothing, wearable sports equipment, foot gear, gloves and combinations thereof. In still yet another embodiment, wherein the sensor is located in an article selected from a group comprising an athlete's uniform, sporting equipment, protective equipment, clothing, wearable sports equipment and combinations thereof. In a further embodiment, wherein the sensor comprises at least one impact sensor and at least one proximity sensor. In still yet another embodiment further comprising a sensor interface unit which is connected to said sensor.

In another embodiment further comprising a central processor unit. In still yet another embodiment further comprising a communication interface unit. In a further embodiment, the central processor unit takes that data from the sensor interface unit to extract information and data regarding an athlete's movements. In yet a further embodiment, the central processor unit takes the data from the nine-axis inertial movement sensor and combines it with the data from the sensor. In yet an additional embodiment, the central processor unit then sends data regarding an athlete's movement to a base station, then the data is displayed on an electronic device. In still a further embodiment, wherein each of the three-axis sensors has a X, Y, and Z axis, one of the axis (Z) aligns with an athlete's spine. In still yet another embodiment, wherein an athlete's movement relative to the Z axis allows the three axis accelerometer to track the athlete's directional movement. In a further embodiment, wherein an athlete's movement relative to the Z axis allows the three axis gyroscope to track the athlete's rotational movement. In a further embodiment, wherein an athlete's movement relative to the Z axis allows the three axis magnetometer to track the athlete's rotational movement by measuring the athlete's orientation relative to the earth's magnetic field. In yet another taekwondo motion tracking apparatus for tracking athletic movement for accurate competitive scoring, the apparatus comprising a nine-axis inertial measurement unit comprising a three axis magnetometer, a three-axis accelerometer and a three-axis gyroscope; an impact sensor; and a proximity sensor, wherein the apparatus determines if a fighter has kicked with a front leg or a back leg when landing a strike on an opponent.

In still another embodiment, wherein said nine-axis inertial measurement unit is located in an article worn by a fighter, the article is selected from a group comprising an athlete's uniform, sporting equipment, protective equipment, clothing, wearable sports equipment, foot gear, gloves and combinations thereof.

In still a further embodiment, a martial arts and boxing motion tracking apparatus for tracking athletic movement for accurate competitive scoring, said apparatus comprising a nine-axis inertial measurement unit comprising a three axis magnetometer, a three-axis accelerometer and a three-axis gyroscope, an impact sensor, and a proximity sensor, wherein the apparatus determines if a fighter has punched with a front arm or a back arm when landing a strike on an opponent. In another embodiment, method for tracking athletic movement for accurate competitive scoring in mixed martial arts, the method comprises providing a nine-axis inertial measurement unit comprising a three axis magnetometer, a three-axis accelerometer and a three-axis gyroscope, an impact sensor; a proximity sensor; and using the nine-axis inertial measurement unit and the sensors to determine if a fighter stuck an opponent with a front leg, back leg, front arm, back arm, and other part of the body.

In yet another embodiment further comprising using the three-axis accelerometer measures directional acceleration of an athlete's movement. In still a further embodiment further comprising using the three axis-gyroscope measures rotational motion of an athlete's movement. In still a further embodiment, the system further comprises using the three axis-magnetometer measures rotational motion of an athlete's movement by measuring the orientation relative to the earth's magnetic field. In yet another embodiment, a method for tracking athletic movement for accurate competitive scoring in freestyle sports, the method comprises providing a nine-axis inertial measurement unit comprising three axis magnetometer, a three-axis accelerometer and a three-axis gyroscope and at least one sensor, and using the nine-axis inertial measurement unit and the sensor to determine an athlete's body position, rate of rotation, and measuring the amount of rotation when performing tricks that require the combined movement of spinning and flipping.

In still yet another embodiment, wherein said free style are selected from a group comprising skiing, snowboarding, figure skating, motor cross, bike riding, snowmobiling, gymnastics, half pipe sports, downhill sports, and any combination thereof. In still a further embodiment further comprising using the three-axis accelerometer measures directional acceleration of an athlete's movement. In yet another embodiment further comprising using the three axis-gyroscope measures rotational motion of an athlete's movement. In yet another embodiment further comprising using the three axis-magnetometer to measure rotational motion of an athlete by measuring orientation relative to earth's magnetic field.

In an embodiment, as an alternative to metallic fiber cloth layers, the participants may use a metallic suit of armor in conjunction with the inner garment containing the hardware for secondary scoring areas. In another embodiment the methods and systems described in paper can be used to qualify and confirm incoming impacts in high impact sports. In a further embodiment, the methods and systems described in this paper can be used to score martial weapons sparring, in which the sensor coil is embedded in the weapon striking surface, and a metallic material is overlaid on the striking target. In yet another embodiment, the methods and systems described in this paper can be used in conjunction with the sport of taekwondo, karate, or the like to detect hand or foot strikes based on contact with metallic material. In yet a further embodiment, the methods and systems described in this paper can be used to detect the angle/location of kicking techniques by placing a metallic material on the bottom of the foot to determine whether a kick was performed with the top or bottom of the foot.

In another embodiment, the methods and systems described in this paper can be used in conjunction with the sport of taekwondo to embed the impedance sensor in the player's hand protector in order to detect impacts to the opponent's body. In a further embodiment, the systems described in this paper can include an inductance sensor embedded in the body and a metallic conductive material placed on the hand protector. In a still another embodiment, the systems and methods described in this paper can be used in conjunction with boxing to score a boxing match.

In another embodiment, the present invention relates to a martial arts gloves with an electronic scoring system: a pair of gloves embedded with at least one metal; at least one metal detector comprising: at least one impedance-based impact sensing mechanism that detects a source of the impact comprising at least one impedance changing mechanism that changes impedance as each of said conductive material is moved towards and away from the impedance changing mechanism as the first participant delivers the impact; at least one impact sensing mechanism using solely piezoelectric which mechanically detects the force of the impact creating electrical charges; at least one impedance-based impact measuring scoring system determining the source of the impact that occurred based on a change in impedance electromagnetically in the impedance changing mechanism, determining the source of an impact prevents scoring impacts that are illegal; at least one impedance changing rate determination engine configured to determine a rate at which the impedance changes in said impedance changing mechanism; at least one impact force determination engine configured to determine a magnitude of a force of the impact based on the rate at which the impedance changes in the impedance changing mechanism and the impedance changing a rate data; and when the gloves approaches said metal detector, the impedance of said detector is changed and the change is picked up and passed to a decision tree.

In yet another embodiment, the metal detector in the gloves is a sensor, and the sensor being selected from a group consisting of an impact sensor, proximity sensor, magnetic proximity sensor, metal detector proximity sensor, three-axis magnetic compass and combinations thereof. In still another embodiment, the sensor in the gloves is located in an article, and the article selected from a group comprising an athlete's uniform, sporting equipment, protective equipment, chest protector, clothing, wearable sports equipment and combinations thereof. In still yet another embodiment, the gloves further comprises an additional sensor, and the additional sensor is selected from a group consisting of an impact sensor, proximity sensor, magnetic proximity sensor, metal detector proximity sensor, three-axis magnetic compass and combinations thereof.

In a further embodiment, the decision tree comprises at least one component for comparing the change to a reference to determine the presence of the punch, at least one noise filter to eliminate invalid changes, and a detector to detect and register valid punches. In yet a further embodiment, the gloves further comprises at least one sensor interface unit which is connected to said additional sensor. In still a further embodiment, the gloves further comprises at least one central processor unit and at least one communication interface unit, and the central processor unit takes that data from said additional sensor interface unit to extract information and data regarding the impact. In still yet a further embodiment, the gloves further comprising a topside and an opposing palm side, at least one adjustable strap to secure the glove to the user's wrist, padding inserted on the topside of the glove, and the metal is embedded on the topside of the glove between the user's knuckles in order that only proper punches will be recorded by the detector. In another embodiment, the gloves are fingerless and further comprises apertures for inserting the user's fingers, additional padding inserted on the opposing palm side of the gloves to allow for open handed blocking, and a portion for protecting the user's thumb, and the thumb portion being absent of metal.

In a further embodiment, the present invention relates to a martial arts gloves with an electronic scoring system: a pair of gloves embedded with at least one an activation material; at least one sensor designed to be activated by said activation material, and the sensor comprising: at least one impedance-based impact sensing mechanism that detects a source of the impact comprising at least one impedance changing mechanism that changes impedance as each of the conductive material is moved towards and away from the impedance changing mechanism as the first participant delivers the impact; at least one impact sensing mechanism using solely piezoelectric which mechanically detects the force of the impact creating electrical charges; at least one impedance-based impact measuring scoring system determining the source of the impact that occurred based on a change in impedance electromagnetically in the impedance changing mechanism, determining the source of an impact prevents scoring impacts that are illegal; at least one impedance changing rate determination engine configured to determine a rate at which the impedance changes in the impedance changing mechanism; at least one impact force determination engine configured to determine a magnitude of a force of the impact based on the rate at which the impedance changes in the impedance changing mechanism and the impedance changing a rate data; and when said gloves approaches said sensor, the impedance of the sensor is changed and the change is picked up and passed to a decision tree, the decision tree comprises at least one component for comparing the change to a reference to determine the presence of the punch, at least one noise filter to eliminate invalid changes, and a detector to detect and register valid punches.

In another further embodiment, the present invention relates to a method of detecting a punch, said method comprises: providing a pair of gloves embedded with at least one activation material; providing at least one sensor designed to be activated by said activation material, the sensor comprising: at least one impedance-based impact sensing mechanism that detects a source of the impact comprising at least one impedance changing mechanism that changes impedance as each of said conductive material is moved towards and away from the impedance changing mechanism as the first participant delivers the impact; at least one impact sensing mechanism using solely piezoelectric which mechanically detects the force of said impact creating electrical charges; at least one impedance-based impact measuring scoring system determining the source of the impact that occurred based on a change in impedance electromagnetically in the impedance changing mechanism, determining the source of an impact prevents scoring impacts that are illegal; at least one impedance changing rate determination engine configured to determine a rate at which the impedance changes in the impedance changing mechanism; at least one impact force determination engine configured to determine a magnitude of a force of the impact based on the rate at which the impedance changes in the impedance changing mechanism and the impedance changing a rate data; and detecting a punch when the gloves approaches said sensor, the impedance of the sensor is changed and the change is picked up and passed to a decision tree and the punch is detected. In an additional embodiment wherein the sensor is selected from a group consisting essentially of impact sensor, proximity sensor, magnetic proximity sensor, metal detector proximity sensor and combinations thereof.

BRIEF DESCRIPTION OF THE DRAWINGS

The accompanying drawings are included to provide a further understanding of the present invention. These drawings are incorporated in and constitute a part of this specification, illustrate one or more embodiments of the present invention and together with the description, serve to explain the principles of the present invention.

FIG. 18 and FIG. 19 show placement of the IMU in taekwondo equipment;

FIG. 23 shows sensor hardware with alternate sensor; and

Among those benefits and improvements that have been disclosed, other objects and advantages of this invention will become apparent from the following description taken in conjunction with the accompanying drawings. The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention that may be embodied in various forms. The figures are not necessarily to scale, some features may be exaggerated to show details of particular components. Therefore, specific structural and functional details disclosed herein are not to be interpreted as limiting, but merely as a basis for the claims and as a representative basis for teaching one skilled in the art to variously employ the present invention.

Figure 1:
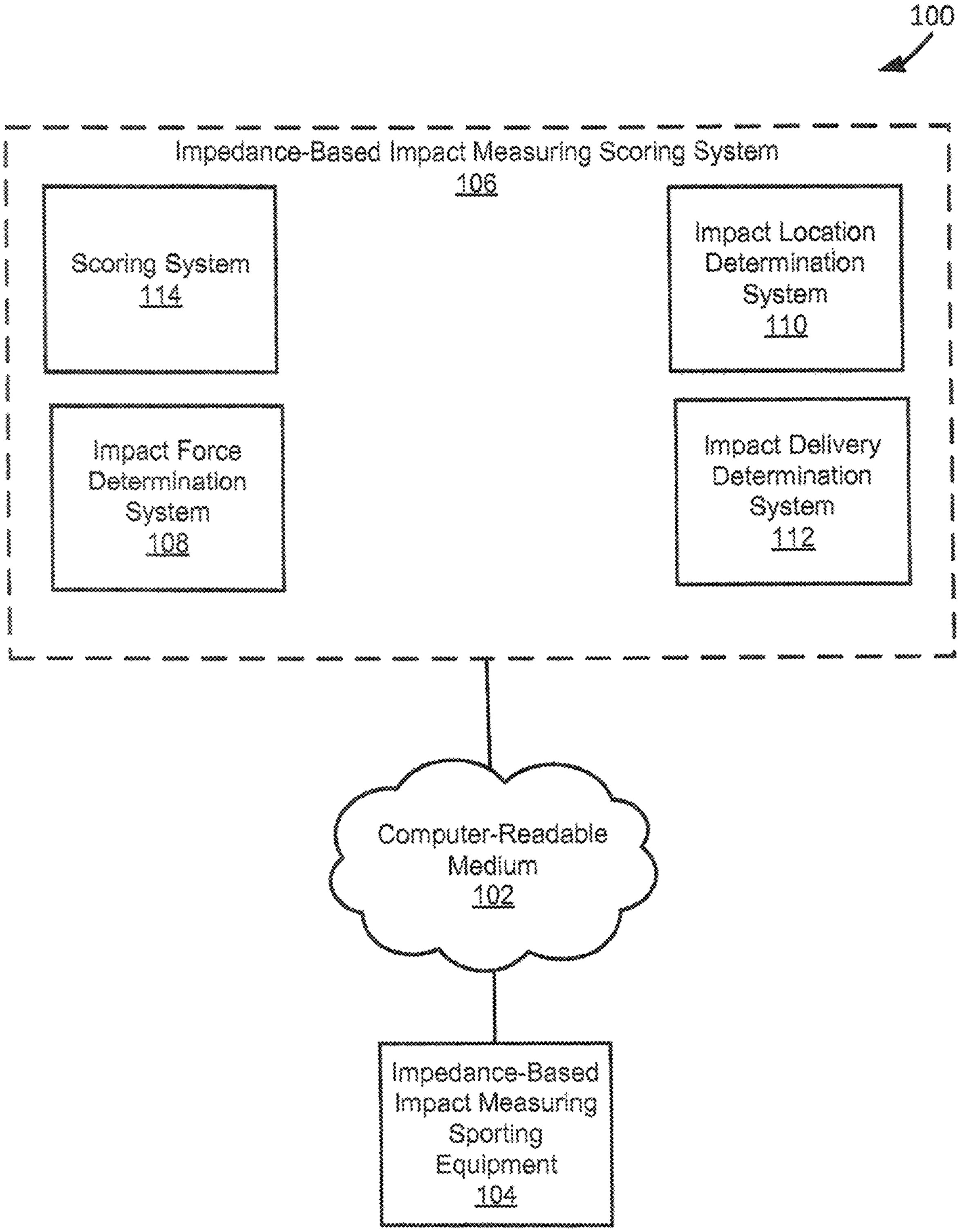
FIG. 1 depicts a diagram of an example of a system for scoring an athletic event using impedance-based impact measuring sporting equipment.

FIG. 1 depicts a diagram 100 of an example of a system for scoring an athletic event using impedance-based impact measuring sporting equipment. The diagram 100 includes a computer-readable medium 102, impedance-based impact measuring sporting equipment 104, and an impedance-based impact measuring scoring system 106. The impedance-based impact measuring sporting equipment 104 and the impedance-based impact measuring scoring system 106 are coupled to each other through the computer-readable medium 102. As used in this paper, a "computer-readable medium" is intended to include all mediums that are statutory (e.g., in the United States, under 35 U.S.C. 101), and to specifically exclude all mediums that are non-statutory in nature to the extent that the exclusion is necessary for a claim that includes the computer-readable medium to be valid. Known statutory computer-readable mediums include hardware (e.g., registers, random access memory (RAM), non-volatile (NV) storage, to name a few), but may or may not be limited to hardware.

The computer-readable medium 102 is intended to represent a variety of potentially applicable technologies. For example, the computer-readable medium 102 can be used to form a network or part of a network. Where two components are co-located on a device, the computer-readable medium 102 can include a bus or other data conduit or plane. Where a first component is co-located on one device and a second component is located on a different device, the computer-readable medium 102 can include a wireless or wired back-end network or LAN. The computer-readable medium 102 can also encompass a relevant portion of a WAN or other network, if applicable. The computer-readable medium 102, the impedance-based impact measuring scoring system 106 and other applicable systems, or devices described in this paper can be implemented as a computer system, a plurality of computer systems, or parts of a computer system or a plurality of computer systems. A computer system, as used in this paper, is intended to be construed broadly. In general, a computer system will include a processor, memory, non-volatile storage, and an interface. A typical computer system will usually include at least a processor, memory, and a device (e.g., a bus) coupling the memory to the processor. The processor can be, for example, a general-purpose central processing unit (CPU), such as a microprocessor, or a special-purpose processor, such as a microcontroller.

The memory can include, by way of example but not limitation, random access memory (RAM), such as dynamic RAM (DRAM) and static RAM (SRAM). The memory can be local, remote, or distributed. The bus can also couple the processor to non-volatile storage. The non-volatile storage is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software on the computer system. The non-volatile storage can be local, remote, or distributed. The non-volatile storage is optional because systems can be created with all applicable data available in memory. Software is typically stored in the non-volatile storage. Indeed, for large programs, it may not even be possible to store the entire program in the memory. Nevertheless, it should be understood that for software to run, if necessary, it is moved to a computer-readable location appropriate for processing, and for illustrative purposes, that location is referred to as the memory in this paper. Even when software is moved to the memory for execution, the processor will typically make use of hardware registers to store values associated with the software, and local cache that, ideally, serves to speed up execution. As used herein, a software program is assumed to be stored at an applicable known or convenient location (from non-volatile storage to hardware registers) when the software program is referred to as "implemented in a computer-readable storage medium." A processor is considered to be "configured to execute a program" when at least one value associated with the program is stored in a register readable by the processor.

In one example of operation, a computer system can be controlled by operating system software, which is a software program that includes a file management system, such as a disk operating system. One example of operating system software with associated file management system software is the family of operating systems known as Windows® from Microsoft Corporation of Redmond, Washington, and their associated file management systems. Another example of operating system software with its associated file management system software is the Linux operating system and its associated file management system. The file management system is typically stored in the non-volatile storage and causes the processor to execute the various acts required by the operating system to input and output data and to store data in the memory, including storing files on the non-volatile storage.

The bus can also couple the processor to the interface. The interface can include one or more input and/or output (I/O) devices. The I/O devices can include, by way of example but not limitation, a keyboard, a mouse or other pointing device, disk drives, printers, a scanner, and other I/O devices, including a display device. The display device can include, by way of example but not limitation, a cathode ray tube (CRT), liquid crystal display (LCD), or some other applicable known or convenient display device. The interface can include one or more of a modem or network interface. It will be appreciated that a modem or network interface can be considered to be part of the computer system. The interface can include an analog modem, isdn modem, cable modem, token ring interface, satellite transmission interface (e.g. "direct PC"), or other interfaces for coupling a computer system to other computer systems. Interfaces enable computer systems and other devices to be coupled together in a network. The computer systems can be compatible with or implemented as part of or through a cloud-based computing system. As used in this paper, a cloud-based computing system is a system that provides virtualized computing resources, software and/or information to client devices. The computing resources, software and/or information can be virtualized by maintaining centralized services and resources that the edge devices can access over a communication interface, such as a network. "Cloud" may be a marketing term and for the purposes of this paper can include any of the networks described herein. The cloud-based computing system can involve a subscription for services or use a utility pricing model. Participants can access the protocols of the cloud-based computing system through a web browser or other container application located on their client device.

A computer system can be implemented as an engine, as part of an engine, or through multiple engines. As used in this paper, an engine includes at least two components: 1) a dedicated or shared processor and 2) hardware, firmware, and/or software modules that are executed by the processor. Depending upon implementation-specific or other considerations, an engine can be centralized or its functionality distributed. An engine can include special purpose hardware, firmware, or software embodied in a computer-readable medium for execution by the processor. The processor transforms data into new data using implemented data structures and methods, such as is described with reference to the FIGURES in this paper. The engines described in this paper, or the engines through which the systems and devices described in this paper can be implemented, can be cloud-based engines.

As used in this paper, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices. As used in this paper, datastores are intended to include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a general- or specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described in this paper.

Datastores can include data structures. As used in this paper, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described in this paper, can be cloud-based datastores. A cloud-based datastore is a datastore that is compatible with cloud-based computing systems and engines.

In an embodiment, the impedance-based impact measuring sporting equipment 104 functions to detect characteristics associated with an impact. In detecting characteristics associated with an impact, the impedance-based impact measuring sporting equipment can include one or a plurality of sensors used in detecting characteristics associated with an impact. Sensors included as part of the impedance-based impact measuring sporting equipment 104 can include any combination of impedance based impact sensing mechanisms, gyroscopes, and/or inertial measurement units (hereinafter referred to as IMUs). Depending upon implementation-specific or other considerations, sensors included as part of the impedance-based impact measuring sporting equipment 104 can be used to measure changes in rotation and location of a participant in an athletic event. Changes in rotation and location, as measured by sensors included as part of the impedance-based impact measuring sporting equipment 104 can be used to measure impacts or magnitudes of forces of impacts, and/or score an athletic event. Further depending upon implementation-specific or other considerations, sensors included as part of the impedance-based impact measuring sporting equipment 104 can be arranged in a sensor matrix.

In another embodiment, the impedance-based impact measuring sporting equipment 104 includes an outer layer of a synthetic elastomeric polymer. Sensors can be embedded in the impedance-based impact measuring sporting equipment. Depending upon implementation-specific or other considerations, in manufacturing the impedance-based impact measuring sporting equipment, sensors can be embedded into a synthetic elastomeric polymer layer in a gel foam. In operation of the impedance-based impact measuring sporting equipment 104, an impact delivered to the impedance-based impact measuring sporting equipment 104 causes the synthetic elastomeric polymer to harden, thereby dispersing energy delivered through the impact across an outer surface or a portion of an outer surface of the impedance-based impact measuring sporting equipment 104. In a further embodiment, the impedance-based impact measuring sporting equipment 104 includes one or a plurality of impedance-based impact sensing mechanisms that function to detect an impact and, e.g., a magnitude of a force of the impact. Depending upon implementation-specific or other considerations, the impedance-based impact measuring sporting equipment 104 can include a set of separate impedance-based impact sensing mechanisms positioned on various portions of a body of a participant using the impedance-based impact measuring sporting equipment 104, or on applicable inanimate objects. In positioning a set of separate impedance-based impact sensing mechanisms on a participant, a portion of the body of the participant of the impedance-based impact measuring sporting equipment 104 where impact occurs can be detected with accuracy sufficient to make the determination useful when scoring an athletic event, or for other applicable purposes where determining the location of a strike is useful.

In yet another embodiment, an impedance-based impact sensing mechanism included as part of the impedance-based impact measuring sporting equipment 104 includes an impedance changing mechanism that changes impedance when a conductive element is moved relative to the impedance changing mechanism and/or when the conductive element comes into contact with the impedance changing mechanism. An impedance changing mechanism can include conductive coils that extend over an area or part of an area of the impedance-based impact sensing mechanism. A regulated AC can be passed through conductive coils that form part of an impedance changing mechanism to form a magnetic field. As a result, when a conductive material moves towards or away from conductive coils of an impedance charging mechanism, currents of varying sizes, e.g. "eddy currents", are induced in the conductive coils that flow opposite the direction that the regulated AC passes through the conductive coils. Currents of varying sizes, induced in an impedance changing mechanism as a conductive material moves towards and away from the impedance changing mechanism, produce counter forces against an original current, e.g. regulated AC, passed through the impedance changing mechanism. As a result, impedance characteristics of an impedance changing mechanism change, e.g. lead to an increased impedance of the impedance changing mechanism, as a conductive material moves towards and away from the impedance changing mechanism.

In still a further embodiment, when a metallic material worn by the striker or striking object approaches an electrically conductive coil with a reference inductance that is included as part of an impedance changing mechanism included as part of the impedance-based impact measuring sporting equipment. The approaching metal changes the inductive value of the coil due to the Eddy current effect. This property can be used to identify the source of the strike which then can be used to qualify an impact of the strike.

In yet another embodiment, an impedance-based impact sensing mechanism included as part of the impedance-based impact measuring sporting equipment 104 includes or is coupled to a digital converter and a data processing system, such as a microprocessor. As a conductive material moves towards an impedance changing mechanism of an impedance-based impact sensing mechanism included as part of the impedance-based impact measuring sporting equipment 104, impedance characteristics of the impedance changing mechanism change. A digital converter included as part of or coupled to the impedance-based impact sensing mechanism generates signals based on changes in impedance in the impedance changing mechanism that can be processed by the data processing system part of or coupled to the impedance-based impact sensing mechanism. Signals generated and processed based on changes in impedance in the impedance changing mechanism can be used to determine impact to an impedance-based impact sensing mechanism of the impedance-based impact measuring sporting equipment 104 and a magnitude of a force of the impact to the impedance-based impact sensing mechanism.

In still a further embodiment, the impedance-based impact measuring sporting equipment 104 includes a plurality of separate impedance changing mechanisms that have different impedance characteristics. In having different impedance characteristics, separate impedance changing mechanisms of the impact measuring sporting equipment can be distinguished from each other using impedance and changing impedance within the separate impedance changing mechanisms. Depending upon implementation-specific or other considerations, in having different impedance characteristics, the separate impedance changing mechanisms can change impedance at different rates when a conductive material is moved towards and away from each separate impedance changing mechanism at the same rate. Further depending upon implementation-specific or other considerations, in having different impedance characteristics, the separate impedance changing mechanisms can have different native impedances, a native impedance, as used in this paper, being an impedance of an impedance changing mechanism when a specific current is run through the impedance changing mechanism without the influence of a conductive material moved in proximity to the impedance changing mechanism. Different impedance characteristics of separate impedance changing mechanisms can be achieved by designing impedance changing mechanisms according to applicable techniques for creating different impedance characteristics in separate impedance changing mechanisms, such as including varying numbers of coils or coils of varying sizes of a conductive material in separate impedance changing mechanisms. In creating impedance-based impact sensing mechanisms that have different impedance characteristics, different parts of the body of a second participant or an applicable inanimate object receiving an impact of a first participant using the impedance-based impact measuring sporting equipment 104 can be detected. For example, based on different impedance characteristics of impedance-based impact sensing mechanisms of the impedance-based impact measuring sporting equipment 104 can be used to determine whether an impact is delivered by a first participant to the chest or the arm of a second participant.

In still yet another embodiment, the impedance-based impact measuring sporting equipment 104 includes a conductive material worn by a first participant delivering an impact to a second participant (or inanimate object). For example, the impedance-based impact measuring sporting equipment 104 can include a conductive material that is positioned on a hand or foot (or other part of the body, such as the elbow, shin, knee, etc.; or on a portion of a weapon) of a first participant using the impedance-based impact measuring sporting equipment 104 to allow an impact delivered against a second participant using of the impedance-based impact measuring sporting equipment 104 to be detected and characteristics, such as the magnitude of the force of the impact, to be determined. The conductive material can be placed in sporting equipment and apparel such as boxing gloves, MMA gloves, gloves, socks, sneakers, shoes, mittens, shirts, pants, shorts, elbow guards, helmets, shin guards, knee pads, striking garments, striking apparel, striking equipment, swords, weapons, and combinations thereof.

In a further embodiment, the impedance-based impact measuring sporting equipment 104 includes separate conductive materials that change impedance differently in impedance-based input sensing mechanisms of a participant wearing the impedance-based input sensing mechanisms. In changing impedances in impedance-based sensing mechanisms differently, separate conductive materials in the impedance-based impact measuring sporting equipment 104, can be of varying sizes or of varying materials. Specific conductive materials in the impedance-based impact measuring sporting equipment 104 can be of varying sizes or varying materials according to a position of specific conductive materials on a first participant using the impedance-based impact measuring sporting equipment 104 to deliver an impact to a second participant (or inanimate object) of the impedance-based impact measuring sporting equipment 104. For example, a conductive material on the foot of a first participant of the impedance-based impact measuring sporting equipment can be of a different size of a conductive material on a hand of the first participant, allowing an impact delivered by the foot of the first participant to be differentiated and subsequently determined from an impact delivered by the hand of the first participant.

In another embodiment, the impedance-based impact measuring scoring system 106 functions to score, at least in part, an athletic event in which the impedance-based measuring sporting equipment 104 is used based on changing impedances of impedance changing mechanisms as a result of impact. In scoring, at least in part, an athletic event, depending upon implementation-specific or other considerations, the impedance-based impact measuring scoring system 106 determines a magnitude of a force of an impact to the impedance-based impact measuring sporting equipment 104 using a change of impedance in an impedance changing mechanism. Further depending upon implementation-specific or other considerations, in scoring, at least in part, an athletic event, the impedance-based impact measuring scoring system 106 can determine a portion of a second participant using the impedance-based impact measuring sporting equipment 104 to which impact is delivered using a change in impedance in an impedance changing mechanism. Depending upon implementation-specific or other considerations, in scoring, at least in part, an athletic event, the impedance-based impact measuring scoring system 106 can determine a portion of a first participant using impedance-based impact measuring sporting equipment 104 that impacts a second participant using impedance-based impact measuring sporting equipment 104 utilizing a change in impedance in an impedance changing mechanism. Further, in scoring, at least in part, an athletic event, depending upon implementation-specific or other considerations, the impedance-based impact measuring scoring system 106 can score the athletic event based on a magnitude of a force of a delivered impact, a portion of a second participant to which the impact is delivered, or a portion of a first participant that delivers the impact to the second participant.

In the example system shown in FIG. 1, the impedance-based impact measuring scoring system 106 includes an impact force determination system 108, an impact location determination system 110, an impact delivery determination system 112, and a scoring system 114. In a specific implementation, the impact force determination system 108 functions to determine a magnitude of a force delivered to a second participant based on a change in impedance in impedance changing mechanisms in the impedance-based impact measuring sporting equipment 104. In determining a magnitude of a force of impact based on a change in impedance in impedance changing mechanisms, the impact force determination system 108 can determine the magnitude of the force of the impact based on the rate at which impedance changes in impedance changing mechanisms as a result of impact. For example, if impedance changes in an impedance changing mechanism at a faster rate as a result of an impact, than a change in impedance in the impedance changing mechanism as a result of a previous impact, then the impact force determination system 108 can determine that a magnitude of a force of the impact is greater than a magnitude of a force of the previous impact. In determining a magnitude of a force of an impact based on rates at which impedance changes in an impedance changing mechanism in the impedance-based impact measuring sporting equipment 104, the impact force determination system 108 can determine the magnitude of the force by comparing the rate at which impedance changes in the impedance changing mechanism to impedance changing rate data for the impedance changing mechanism. Impedance changing rate data for an impedance changing mechanism of the impedance-based impact measuring sporting equipment 104 can be predetermined and specify magnitudes of forces of impact corresponding to specific rates.

In another embodiment, the impact location determination system 110 functions to determine a portion of a second participant (or inanimate object) of the impedance-based impact measuring sporting equipment 104 at which an impact occurs. In determining a portion of a second participant of the impedance-based impact measuring sporting equipment 104 at which an impact occurs, the impact location determination system 110 can determine the portion of the second participant based on impedance characteristics specific to an impedance changing mechanism positioned on the body of the second participant. For example, the impact location determination system 110 can determine that an impact occurs in the chest of a second participant using impedance-based impact measuring sporting equipment 104 based on impedance characteristics of specific impedance changing mechanisms included as part of the impedance-based impact measuring sporting equipment 104. Depending upon implementation-specific or other considerations, the impact location determination system 110 can determine a specific impedance changing mechanism on a second participant based on rates at which impedance in the impedance changing mechanisms changes when a conductive material is moved towards and away from the impedance changing mechanism. Further depending upon implementation-specific or other considerations, the impact location determination system 110 can determine a specific impedance changing mechanism based on a native impedance of the specific changing mechanism included as part of the impedance-based impact measuring sporting equipment 104.

In still another embodiment, the impact delivery determination system 112 functions to determine a portion of a first participant using the impedance-based impact measuring sporting equipment 104 that delivers an impact to a second participant using the impedance-based impact measuring sporting equipment 104. For example, the impact delivery determination system 112 can determine that an impact is delivered by a foot or a hand of a first participant. In determining a portion of a first participant that delivers an impact, the impact delivery determination system 112 can use impact delivery characteristics data of a first participant using the impedance-based impact measuring sporting equipment 104. Impact delivery characteristics data of a first participant using the impedance-based impact measuring sporting equipment 104 can specify a rate at which impedance changes in impedance changing mechanisms as a result of conductive materials positioned at different positions on a first participant being moved towards and away from the impedance changing mechanisms. Specifically, impedance delivery characteristics data are different for conductive materials of different sizes or materials that are positioned at different portions of a participant, e.g. a foot or a hand of the participant. Using a rate at which impedance changes in an impedance changing mechanism of a first participant using the impedance-based impact measuring sporting equipment 104 as a result of an impact to the impedance changing mechanism, and impact delivery characteristics, the impact delivery determination system 112 can determine a portion of a first participant that delivers the impact to a second participant. For example, the impact delivery determination system 112 can determine, based on the rate at which impedance changes in an impedance changing mechanism and impact delivery characteristics, that a foot of a first participant delivered impact to a second participant using the impedance-based impact measuring sporting equipment 104.

In a further embodiment, the scoring system 114 functions to score an athletic event in response to impacts received and delivered by wearers of the impedance-based impact measuring sporting equipment. For example, the scoring system 114 can score an athletic event based on where an impact is received, a magnitude of the force of the impact, and/or a portion of a first participant that delivers the impact. Further, the scoring system 114 can score an athletic event based on impact scoring data for an athletic event. Impact scoring data for an athletic event can specify how to score, e.g. a number of points to award a first participant, based on where an impact is delivered, a magnitude of a force of the impact, a portion of a user that delivers the impact, or other discernible factors.

In still a further embodiment, the scoring system 114 can score an athletic event based on impact scoring data and a magnitude of a force of a delivered impact, as determined by the impact location determination system 108. Specifically, impact scoring data can specify to award a specific number of points based on a magnitude of the force of a delivered impact. As a result, the scoring system 114 can award a number of points as specified by impact scoring data to a first participant who delivers an impact based on a magnitude of a force of the impact, as determined by the impact force determination system 108. In yet another embodiment, the scoring system 114 can score an athletic event based on impact scoring data and a portion of a second participant to which an impact is delivered, as determined by the impact location determination system 110. For example, impact scoring data can specify to award a specific number of points based on a portion of a second participant to which an impact is delivered, e.g. award more points if an impact is delivered to a chest of a second participant as opposed to a leg. As a result, the scoring system 114 can award a number of points as specified by the impact scoring data to a first participant who delivers an impact based on a portion of a second participant to which the impact is delivered, as determined by the impact location determination system 110.

In still another embodiment, the scoring system 114 can score an athletic event based on impact scoring data and a portion of a first participant that delivers an impact to a second participant, as determined by the impact delivery determination system 112. For example, impact scoring data can specify to award a specific number of points based on a portion of a first participant that delivers an impact to a second participant, e.g. award more points if an impact is delivered by the foot of a first participant as opposed to a hand of the first participant. As a result, the scoring system 114 can award a number of points as specified by the impact scoring data to a first participant who delivers an impact based on a portion of the first participant that delivers the impact to a second participant, as determined by the impact delivery determination system 112.

Figure 2:
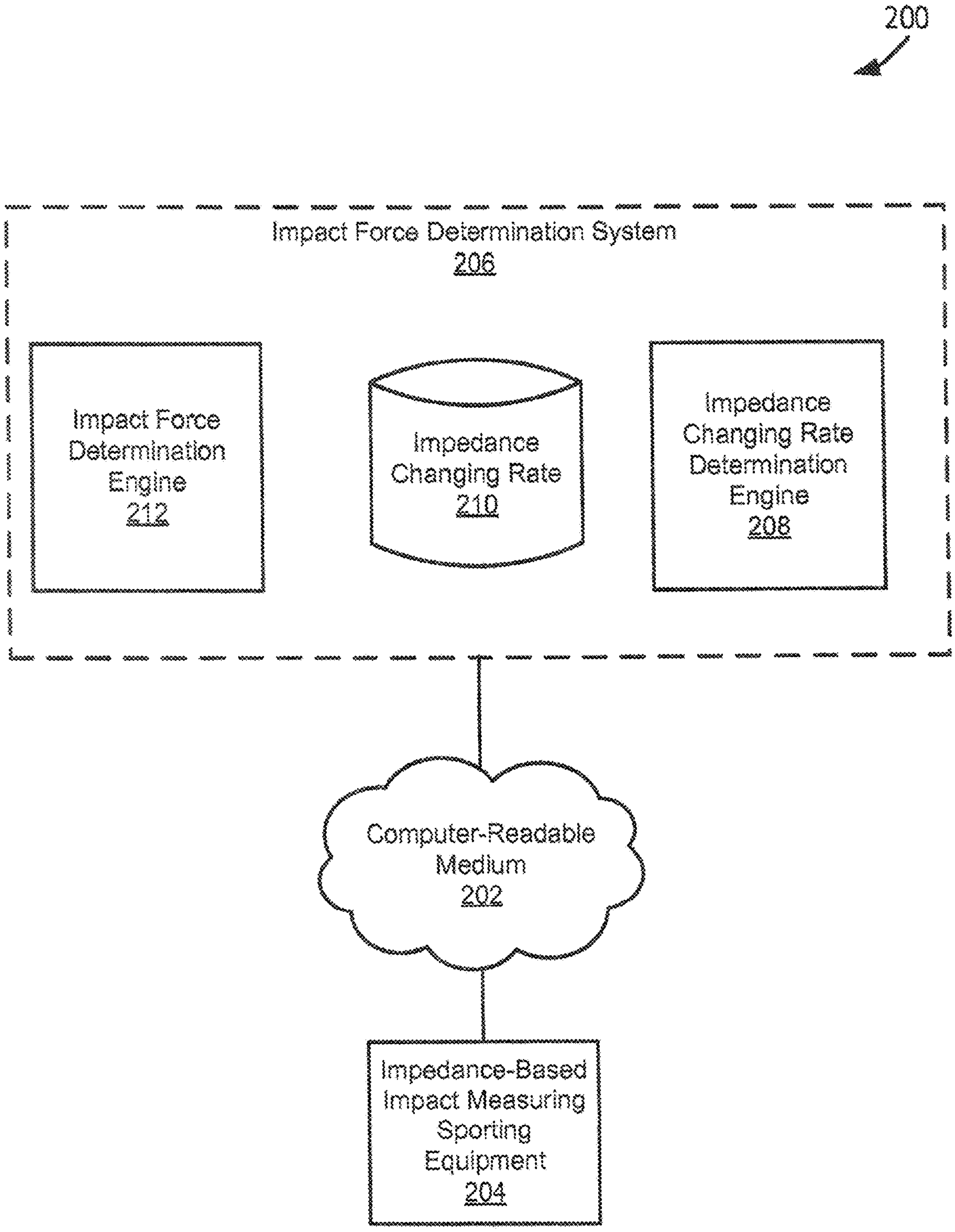
FIG. 2 depicts a diagram of an example of a system for determining a magnitude of a force of an impact based on the rate at which impedance changes in impedance-based impact measuring sporting equipment.

FIG. 2 depicts a diagram 200 of an example of a system for determining a magnitude of a force of an impact based on the rate at which impedance changes in impedance-based impact measuring sporting equipment. The example system shown in FIG. 2 includes a computer-readable medium 202, an impedance-based impact measuring sporting equipment 204, and an impact force determination system 206. In the example system shown in FIG. 2, the impedance-based impact measuring sporting equipment 204 and the impact force determination system 206 are coupled to each other through the computer-readable medium 202.

In a specific implementation, the impedance-based impact measuring sporting equipment 204 functions according to an applicable device for sensing impact in an athletic event using an impedance-based impact sensing mechanism, such as the impedance-based impact measuring sporting equipment described in this paper. Depending upon implementation-specific or other considerations, the impedance-based impact measuring sporting equipment 204 can include one or a plurality of impedance changing mechanisms positioned on various portions of a body of a wearer of the impedance-based impact measuring sporting equipment 204. Impedance changing mechanisms included as part of the impedance-based impact measuring sporting equipment 204 can change impedance as a conductive material is moved towards and away from the impedance changing mechanisms and/or comes into contact with the impedance changing mechanisms. In operation, a conductive material can be moved toward an impedance changing mechanism included as part of the impedance-based impact measuring sporting equipment 204, when an impact is delivered to a wearer of the impedance-based impact measuring sporting equipment.

In another embodiment, the impact force determination system 206 functions according to an applicable system for determining a magnitude of a force of an impact, such as the impact force determination systems described in this paper. Depending upon implementation-specific or other considerations, the impact force determination system 206 can determine a magnitude of an impact force determination system delivered to a wearer of the impedance-based impact measuring sporting equipment 204 based on a rate at which impedance changes in an impedance changing mechanism included as part of the impedance-based impact measuring sporting equipment 204. Further depending upon implementation-specific or other considerations, the impact force determinations system can determine a force of an impact delivered to a wearer of the impedance-based impact measuring sporting equipment 204 based on a mechanism for measuring an acceleration of the impedance-based impact measuring sporting equipment 204, such as an accelerometer, as a result of a delivered impact.

In the example system shown in FIG. 2, the impact force determination system 206 includes an impedance changing rate determination engine 208, an impedance changing rate datastore 210, and an impact force determination engine 212. In a specific implementation, the impedance changing rate determination engine 208 functions to determine a rate at which impedance changes in an impedance changing mechanism included as part of the impedance-based impact measuring sporting equipment 204. The impedance changing rate determination engine 208 can determine a rate at which impedance changes in an impedance changing mechanism as a conductive material is moved towards and comes into contact with the impedance changing mechanism included in the impedance-based impact measuring sporting equipment 204. The moving of a conductive material towards and into contact with an impedance changing mechanism included in the impedance-based impact measuring sporting equipment can correspond to a wearer, e.g. a user or inanimate object, of the impedance-based impact measuring sporting equipment 204 receiving an impact from another wearer of the impedance-based impact measuring sporting equipment 204.

In yet a further embodiment, the impedance changing rate determination engine 208 functions to determine an impedance in an impedance changing mechanisms included in the impedance-based impact measuring sporting equipment 204 based on a signal originated by or received from an impedance-based impact sensing mechanism. Depending upon implementation-specific or other considerations, a signal received from an impedance-based impact sensing mechanism by the impedance changing rate determination engine 208 includes impedances of an impedance changing mechanism over a specific amount of time. Further depending upon implementation-specific or other considerations, a signal received from an impedance-based impact sensing mechanism by the impedance changing rate determination engine 208 includes a current through an impedance changing mechanism or a voltage across the impedance changing mechanism as an impedance of the impedance changing mechanism changes over a specific amount of time. The impedance changing rate determination engine 208 can determine impedance change rates of an impedance changing mechanism based on a signal received from a digital converter that is part of or coupled to an impedance-based impact sensing mechanism that includes the impedance changing mechanism. Depending upon implementation-specific or other considerations, a signal received from a digital converter by the impedance changing rate determination engine 208 includes impedances of an impedance changing mechanism over a specific amount of time. Further depending upon implementation-specific or other considerations, a signal received form a digital converter by the impedance changing rate determination engine 208 includes a current through an impedance changing mechanism or a voltage across the impedance changing mechanism as an impedance of the impedance changing mechanism changes over a specific amount of time.

In still another embodiment, the impedance changing rate determination engine 208 functions to determine impedance changing rates of an impedance changing mechanism based on determined impedances of the impedance changing mechanism over a specific period of time. For example, the impedance changing rate determination engine 208 can determine a first impedance at a first specific time in a specific period of time and a second impedance at a second specific time in the specific period of time after the first specific time to determine an impedance changing rate of the impedance changing mechanism. Depending upon implementation-specific or other considerations, an impedance changing rate of an impedance changing mechanism, as determined by the impedance changing rate determination engine 208 varies over a specific period of time.

In still a further embodiment, the impedance changing rate datastore 210 functions to store impedance changing rate data. Impedance changing rate data stored in the impedance changing rate datastore 210 can include a specific force that is delivered to a specific impedance changing mechanism that corresponds to a specific rate at which impedance changes in the specific impedance changing mechanism. Impedance changing rate data stored in the impedance changing rate datastore 210 can be specific to impedance changing mechanisms included in the impedance-based impact measuring sporting equipment 204. For example, a first impedance changing mechanism can change impedance at a different rate from a second impedance changing mechanism, as reflected by impedance changing rate data stored in the impedance changing rate datastore 210.

In another embodiment, the impact force determination engine 212 functions to determine a magnitude of a force of an impact delivered to an impedance-based impact measuring sporting equipment 204. The impact force determination engine 212 can determine a magnitude of a force delivered to impedance-based impact measuring sporting equipment 204 based on an impedance changing rate of an impedance changing mechanism, as determined by the impedance changing rate determination engine 208. The impact force determination engine 212 can also determine a magnitude of force delivered to impedance-based impact measuring sporting equipment based on impedance changing rate data stored in the impedance changing rate datastore 210. For example, the impact force determination engine 212 can look up impedance changing rates and corresponding magnitude of force of impact for a specific impedance changing mechanism included as part of impedance changing rate data stored in the impedance changing rate datastore 210 and impedance changing rates for the specific impedance changing mechanism to determine a magnitude of a force of an impact delivered to an impedance-based impact sensing mechanism that includes the specific impedance changing mechanism.

Figure 3:
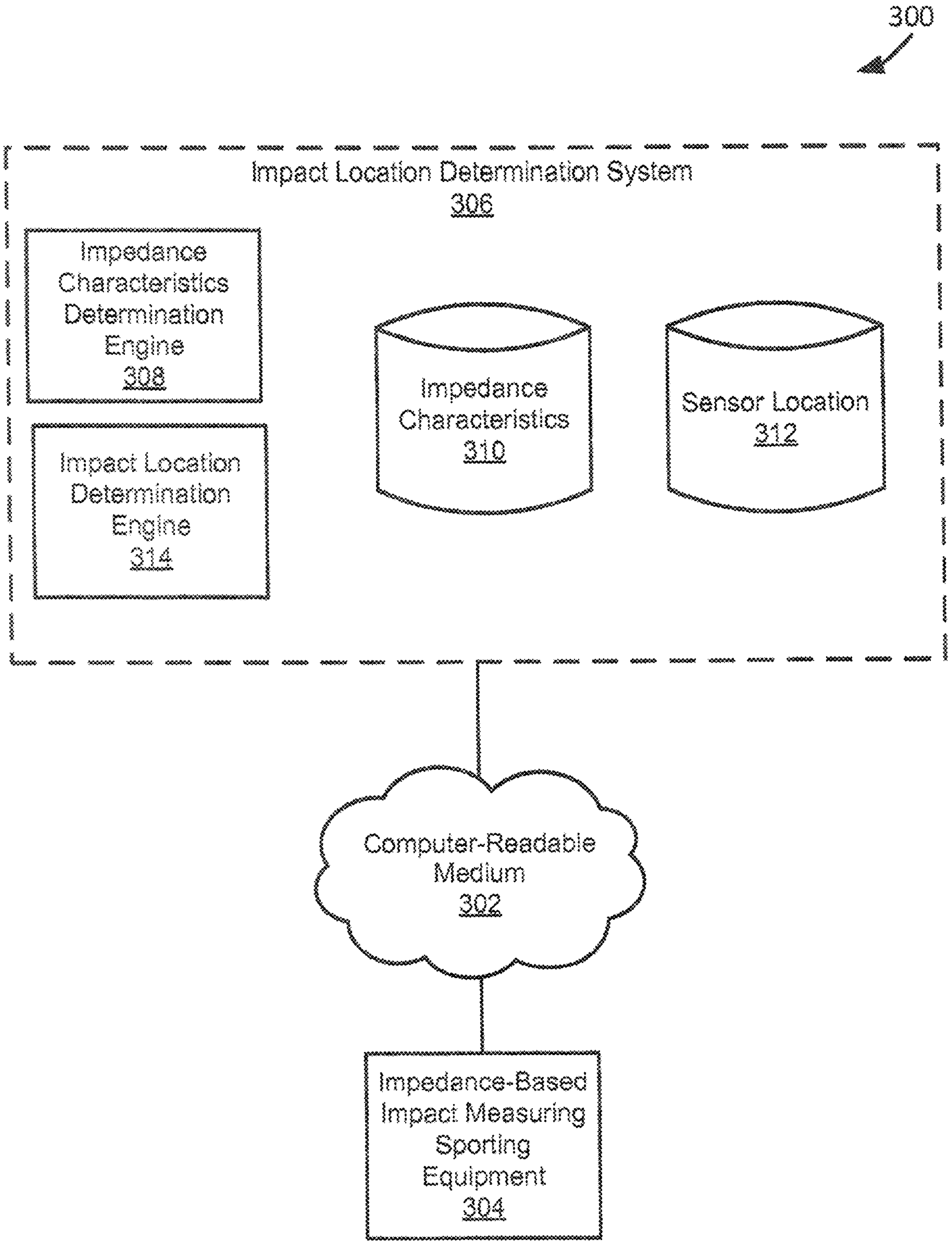
FIG. 3 depicts a diagram of a system for determining a location on a participant to which an impact is delivered.

FIG. 3 depicts a diagram 300 of a system for determining a location on a participant to which an impact is delivered. The example system shown in FIG. 3 includes a computer-readable medium 302, an impedance-based impact measuring sporting equipment 304, and an impact location determination system 306. In the example system shown in FIG. 3, the impedance-based impact measuring sporting equipment 304 and the impact location determination system 306 are coupled to each other through the computer-readable medium 302.

In yet another embodiment, the impedance-based impact measuring sporting equipment 304 functions according to an applicable device for sensing impact in an athletic event using an impedance-based impact sensing mechanism, such as the impedance-based impact measuring sporting equipment described in this paper. Depending upon implementation-specific or other considerations, the impedance-based impact measuring sporting equipment 304 can include one or a plurality of impedance changing mechanisms positioned on various portions of a body of a wearer of the impedance-based impact measuring sporting equipment 304. Impedance changing mechanisms included as part of the impedance-based impact measuring sporting equipment 304 can change impedance as a conductive material is moved towards and away from the impedance changing mechanisms and/or comes into contact with the impedance changing mechanisms. In operation, a conductive material can be moved toward an impedance changing mechanism included as part of the impedance-based impact measuring sporting equipment 304, when an impact is delivered to a wearer of the impedance-based impact measuring sporting equipment.

In a further embodiment, the impact location determination system 306 functions according to an applicable system for determining a location on a participant using the impedance-based impact measuring sporting equipment to which an impact is delivered, such as the impact location determination systems described in this paper. A participant for which the impact location determination system 306 determines where an impact is delivered can be a person or an inanimate object. An impact, for which the impact location determination system 306 determines where the impact is delivered, can be delivered by a participant using impedance-based impact measuring sporting equipment 304. Specifically, a participant using impedance-based impact measuring sporting equipment can include a conductive material that is moved towards an impedance-based impact sensing mechanism as an impact is delivered. The impact location determination system 306 can determine an location on a participant to which an impact is delivered based on impedance characteristics of impedance changing mechanisms in an impedance-based impact sensing mechanism, to which the impact is delivered or in proximity to a location on the participant to which the impact is delivered. In the example system shown in FIG. 3, the impact location determination system 306 includes an impedance characteristics determination engine 308, an impedance characteristics datastore 310, a sensor location datastore 312 and an impact location determination engine 314.

In a specific implementation, the impedance characteristics determination engine 308 functions to determine impedance characteristics of an impedance changing mechanism in an impedance-based impact sensing mechanism. An impedance-based impact sensing mechanism including an impedance changing mechanism for which the impedance characteristics determination engine 308 determines impedance characteristics for can directly receive an impact or be in proximity to a location on a participant that receives the impact. Impedance characteristics determined by the impedance characteristics determination engine 308 can include a native impedance of an impedance changing mechanism, a rate at which impedance changes in an impedance changing mechanism, or an impedance value that an impedance in the impedance changing mechanism changes to as a result of a conductive material moved towards and away from the impedance changing mechanism.

In yet another embodiment, the impedance characteristics datastore 310 functions to store impedance characteristics data of impedance changing mechanisms included in impedance-based impact sensing mechanisms as part of the impedance-based impact measuring sporting equipment 304. Impedance characteristics data can include a native impedance of an impedance changing mechanism, a rate at which impedance changes in an impedance changing mechanism, or an impedance value that an impedance in the impedance changing mechanism changes to as a result of a conductive material moved towards and away from the impedance changing mechanism. Impedance characteristics data can be unique to each impedance-based impact sensing mechanism such that impedance changing mechanisms of the impedance-based impact sensing mechanisms have different impedance characteristics. For example, impedance changing mechanisms in different impedance-based impact sensing mechanisms can have a different native impedance or change impedances at different rates. Impedance characteristics data stored in the impedance characteristics datastore 310 can also include an identification of each impedance-based impact sensing mechanism that includes impedance changing mechanisms with corresponding impedance characteristics.

In another embodiment, the sensor location datastore 312 functions to store sensor location data. Sensor location data can include the location, on a participant using the impedance-based impact measuring sporting equipment, that each impedance-based impact sensing mechanism is located. For example, sensor location data stored in the sensor location datastore 312 can specify that a specific impedance-based impact sensing mechanism is positioned on a chest of a participant of the impedance-based impact measuring sporting equipment 304.

In a further embodiment, the impact location determination engine 314 functions to determine a location on a participant at which an impact is delivered. In determining an impact location, the impact location determination engine 314 can determine a specific impedance-based impact sensing mechanism that either receives an impact or is in proximity to a location that receives an impact. The impact location determination engine 314 can determine a specific impedance-based impact sensing mechanism based on impedance characteristics of an impedance changing mechanism in the specific impedance-based impact sensing mechanism, as determined by the impedance characteristics determination engine 308 and impedance characteristics data stored in the impedance characteristics datastore 310. The impact location determination engine 314 can determine a location of a specific impedance-based impact sensing mechanism, and thereby a location on a participant at which an impact is delivered, using sensor location data stored in the sensor location datastore 312.

Figure 4:
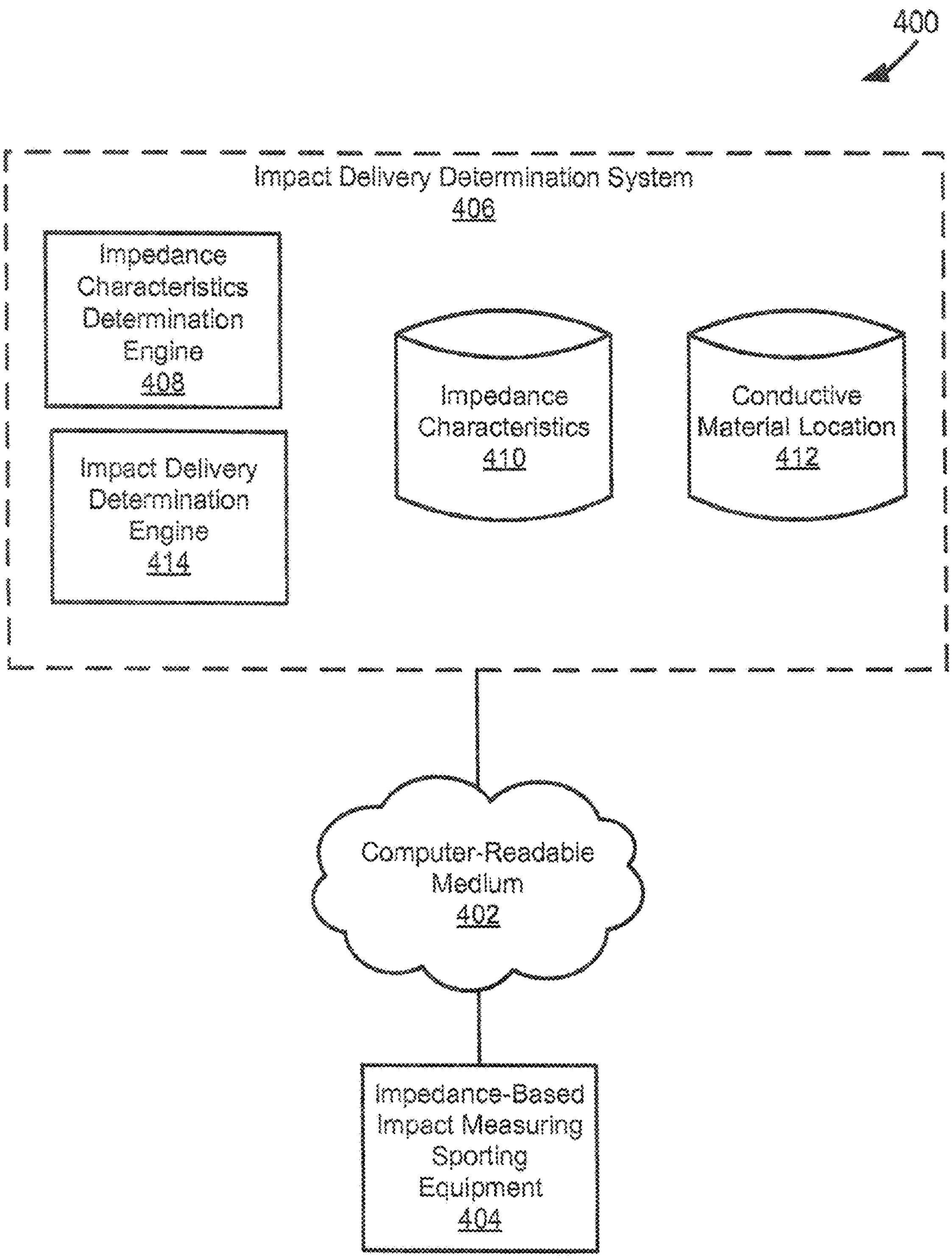
FIG. 4 depicts a diagram of an example of a system for determining a portion of participant that delivers an impact to another participant using impedance-based impact measuring sporting equipment.

FIG. 4 depicts a diagram 400 of an example of a system for determining a portion of a participant that delivers an impact to another participant using impedance-based impact measuring sporting equipment. The example system shown in FIG. 4 includes a computer-readable medium 402, an impedance-based impact measuring sporting equipment 404, and an impact delivery determination system 406. In the example system shown in FIG. 4, the impedance-based impact measuring sporting equipment 404 and the impact delivery determination system 406 are coupled to each other through the computer-readable medium 402. In yet another embodiment, the impedance-based impact measuring sporting equipment 404 functions according to an applicable device for sensing impact in an athletic event using an impedance-based impact sensing mechanism, such as the impedance-based impact measuring sporting equipment described in this paper. Depending upon implementation-specific or other considerations, the impedance-based impact measuring sporting equipment 404 can include one or a plurality of impedance changing mechanisms positioned on various portions of a body of a wearer of the impedance-based impact measuring sporting equipment 404. Impedance changing mechanisms included as part of the impedance-based impact measuring sporting equipment 404 can change impedance as a conductive material is moved towards and away from the impedance changing mechanisms and/or comes into contact with the impedance changing mechanisms. In operation, a conductive material can be moved toward an impedance changing mechanism included as part of the impedance-based impact measuring sporting equipment 404, when an impact is delivered to a wearer of the impedance-based impact measuring sporting equipment.

In yet a further embodiment, the impact delivery determination system 406 functions according to an applicable system for determining a location on a participant that delivers an impact to another participant using the impedance-based impact measuring sporting equipment, such as the impact delivery determination systems described in this paper. A location on a participant that delivers an impact can be delivered by the participant using impedance-based impact measuring sporting equipment 404. Specifically, a participant using impedance-based impact measuring sporting equipment can include conductive material placed on various portions of the participant's body that can be moved towards an impedance-based impact sensing mechanism as an impact is delivered to another participant. The impact delivery determination system 406 can determine a location on a participant that delivers an impact based on impedance characteristics of an impedance changing mechanism included in an impedance-based impact sensing mechanism that receives an impact or is proximal to a location on a participant that receives the impact.

In the example system shown in FIG. 4, the impact delivery determination system 406 includes an impedance characteristics determination engine 408, an impedance characteristics datastore 410, an conductive material location datastore 412, and an impact delivery determination engine 414. In a specific implementation, the impedance characteristics determination engine 408 functions according to an applicable system for determining impedance characteristics of an impedance changing mechanism, such as the impedance characteristics determination engines described in this paper. Impedance characteristics determined by the impedance characteristics determination engine 408 can include the rate at which impedance changes in an impedance changing mechanism as a specific conductive material is moved towards and away from the impedance changing mechanism. A rate at which impedance changes can be specific to a conductive material that is moved towards and away from the impedance changing mechanism. For example, a rate at which an impedance changes in an impedance changing mechanism can be different for a conductive material positioned on a foot of a participant than a conductive material positioned on a hand of a participant, as the respective foot or hand is moved towards and away from the impedance changing mechanism.

In another embodiment, the impedance characteristics datastore 410 functions according to an applicable datastore for storing impedance characteristics, such as the impedance characteristics datastores described in this paper. The impedance characteristics datastore 410 can store impedance characteristics data that includes rates at which impedance changes in impedance changing mechanisms as a specific conductive material is moved towards and away from the impedance changing mechanism. Impedance characteristics data can also include an identification of specific conductive materials corresponding to rates at which impedance changes in impedance changing mechanisms. For example if a specific conductive material causes impedance to change in an impedance changing mechanism at a first rate, then impedance characteristics data can include an identification of the specific conductive material and the rate at which it causes impedance to change.

In still a further embodiment, the conductive material location datastore 412 functions to store conductive material location data. Conductive material location data can indicate where on a participant specific conductive materials are located. For example, conductive material location data stored in the conductive material location datastore 412 can indicate that a first conductive material is located on a foot of a participant and that a second conductive material is located on a hand of the participant.

In yet another embodiment, the impact delivery determination engine 414 functions to determine a portion of a participant that delivers an impact to another participant using the impedance-based impact measuring sporting equipment 404. For example, the impact delivery determination engine 414 can determine that a foot of a participant delivers an impact to another participant. In determining a portion of a participant that delivers an impact, the impact delivery determination engine 414 can determine a specific conductive material that delivers or is in proximity to a portion of the participant that delivers the impact. The impact delivery determination engine 414 can determine a specific conductive material based on impedance characteristics of an impedance changing mechanism included in an impedance-based impact sensing mechanism that receives an impact or is in proximity to a location on a participant that receives the impact. For example, the impact delivery determination engine 414 can use the rate at which impedance changes in an impedance changing mechanism, as determined by the impedance characteristics determination engine 408, and impedance characteristics data stored in the impedance characteristics datastore 410 to determine a specific conductive material. The impact delivery determination engine 414 can determine a portion of a user that delivers an impact based on a determined specific conductive material and conductive material location data stored in the conductive material location datastore 412.

Figure 5:
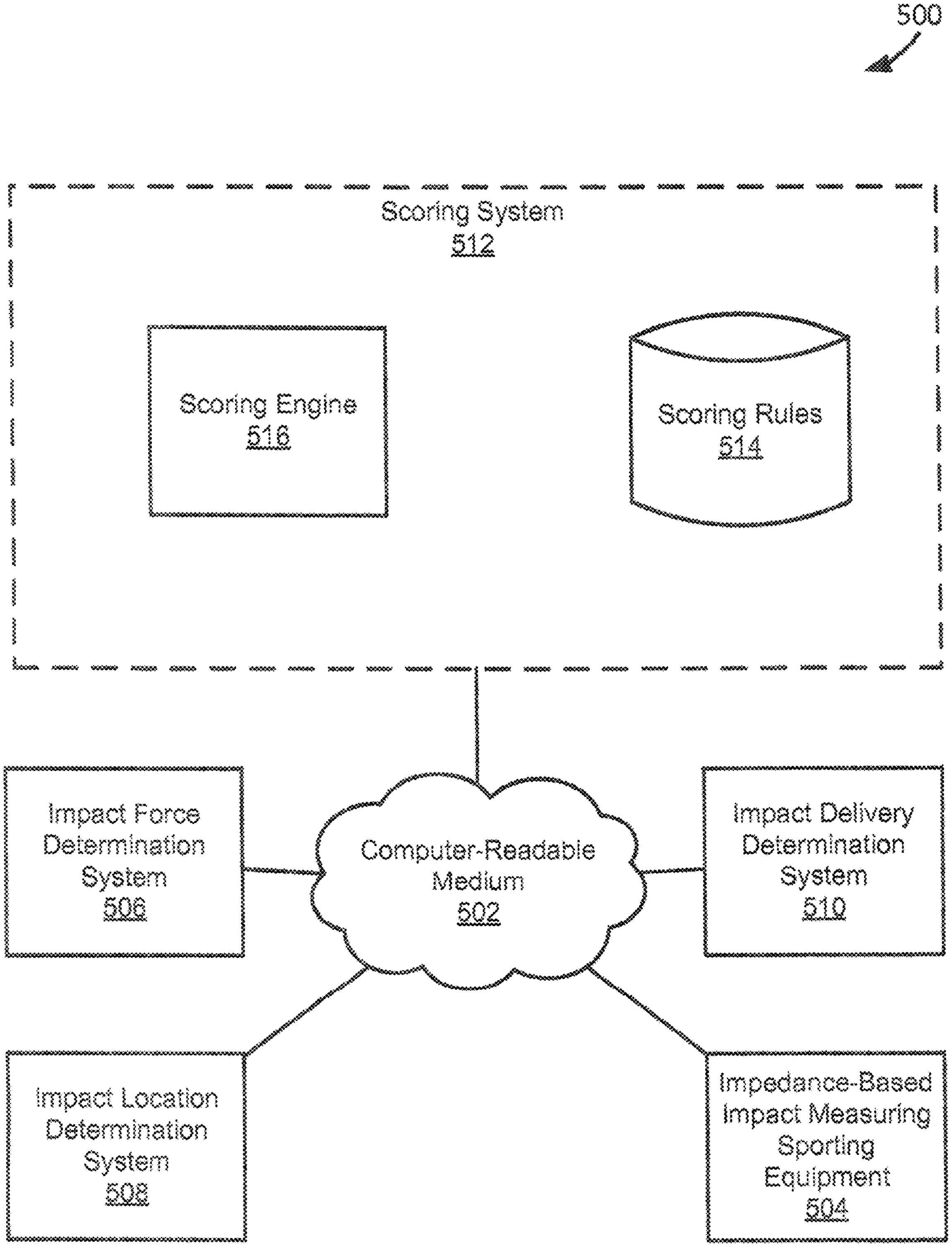
FIG. 5 depicts a diagram of an example of a system for scoring an athletic event based on impacts received by impedance-based impact measuring sporting equipment.

FIG. 5 depicts a diagram 500 of an example of a system for scoring an athletic event based on impacts received by impedance-based impact measuring sporting equipment. The example system shown in FIG. 5 includes a computer-readable medium 502, an impedance-based impact measuring sporting equipment 504, an impact force determination system 506, an impact location determination system 508, an impact delivers determination system 510, and a scoring system 512. In the example system shown in FIG. 5, the impedance-based impact measuring sporting equipment 504, the impact force determination system 506, the impact location determination system 508, the impact delivery determination system 510, and the scoring system 512 are coupled to each other through the computer-readable medium 502.

In another embodiment, the impedance-based impact measuring sporting equipment 504 functions according to an applicable device for sensing impact in an athletic event using an impedance-based impact sensing mechanism, such as the impedance-based impact measuring sporting equipment described in this paper. Depending upon implementation-specific or other considerations, the impedance-based impact measuring sporting equipment 504 can include one or a plurality of impedance changing mechanisms positioned on various portions of a body of a wearer of the impedance-based impact measuring sporting equipment 504. Impedance changing mechanisms included as part of the impedance-based impact measuring sporting equipment 504 can change impedance as a conductive material is moved towards and away from the impedance changing mechanisms and/or comes into contact with the impedance changing mechanisms. In operation, a conductive material can be moved toward an impedance changing mechanism included as part of the impedance-based impact measuring sporting equipment 504, when an impact is delivered to a wearer of the impedance-based impact measuring sporting equipment.

In still another embodiment, the impact force determination system 506 functions according to an applicable system for determining a magnitude of a force of an impact, such as the impact force determination systems described in this paper. Depending upon implementation-specific or other considerations, the impact force determination system 506 can determine a magnitude of an impact force determination system delivered to a wearer of the impedance-based impact measuring sporting equipment 504 based on a rate at which impedance changes in an impedance changing mechanism included as part of the impedance-based impact measuring sporting equipment 504. Further depending upon implementation-specific or other considerations, the impact force determinations system can determine a force of an impact delivered to a wearer of the impedance-based impact measuring sporting equipment 504 based on a mechanism for measuring an acceleration of the impedance-based impact measuring sporting equipment 504, such as an accelerometer, as a result of a delivered impact.

In a specific implementation, the impact location determination system 508 functions according to an applicable system for determining a location on a participant using the impedance-based impact measuring sporting equipment to which an impact is delivered, such as the impact location determination systems described in this paper. A participant for which the impact location determination system 508 determines where an impact is delivered can be a person or an inanimate object. An impact, for which the impact location determination system 508 determines where the impact is delivered, can be delivered by a participant using impedance-based impact measuring sporting equipment 504. Specifically, a participant using impedance-based impact measuring sporting equipment can include a conductive material that is moved towards an impedance-based impact sensing mechanism as an impact is delivered. The impact location determination system 508 can determine an location on a participant to which an impact is delivered based on impedance characteristics of impedance changing mechanisms in an impedance-based impact sensing mechanism, to which the impact is delivered or in proximity to a location on the participant to which the impact is delivered.

In yet another embodiment, the impact delivery determination system 510 functions according to an applicable system for determining a location on a participant that delivers an impact to another participant using the impedance-based impact measuring sporting equipment, such as the impact delivery determination systems described in this paper. A location on a participant that delivers an impact can be delivered by the participant using impedance-based impact measuring sporting equipment 504. Specifically, a participant using impedance-based impact measuring sporting equipment can include conductive material placed on various portions of the participant's body that can be moved towards an impedance-based impact sensing mechanism as an impact is delivered to another participant. The impact delivery determination system 510 can determine a location on a participant that delivers an impact based on impedance characteristics of an impedance changing mechanism included in an impedance-based impact sensing mechanism that receives an impact or is proximal to a location on a participant that receives the impact.

In a further embodiment, the scoring system 512 functions according to an applicable system for scoring an athletic event using impedance-based impact measuring sporting equipment, such as the scoring systems described in this paper. Depending upon implementation-specific or other considerations, the scoring system 512 can score an athletic event based on any combination of a magnitude of a force of an impact delivered during the athletic event, a location at which the impact is delivered, and a portion of a participant that delivers the impact.

In the example system shown in FIG. 5, the scoring system 512 includes a scoring rules datastore 514 and a scoring engine 516. In a specific implementation, the scoring rules datastore 514 functions to store scoring rules for an athletic event. Scoring rules can specify how to score an event based on any combination of a magnitude of a force of an impact delivered during the athletic event, a location at which the impact is delivered, and a portion of a participant that delivers the impact. For example, scoring rules can specify to award three points if an impact is delivered by a foot of a participant to the chest of another participant with a magnitude of force greater than a specific value. In another embodiment, the scoring engine 516 functions to score an athletic event. The scoring engine 516 can score an athletic event based on scoring rules stored in the scoring rules datastore 514, and any combination of a magnitude of a force of an impact delivered during the athletic event, a location at which the impact is delivered, and a portion of a participant that delivers the impact. For example, if scoring rules specify to award three points if an impact is delivered by a foot of a participant to a chest of another participant with a magnitude of force greater than a specific value, and if it is determined that an impact is in fact delivered by the foot of the participant to the chest of another participant with a magnitude of force greater than a specific value, then the scoring engine 516 can award three points to the participant who delivered the impact.

Figure 6:
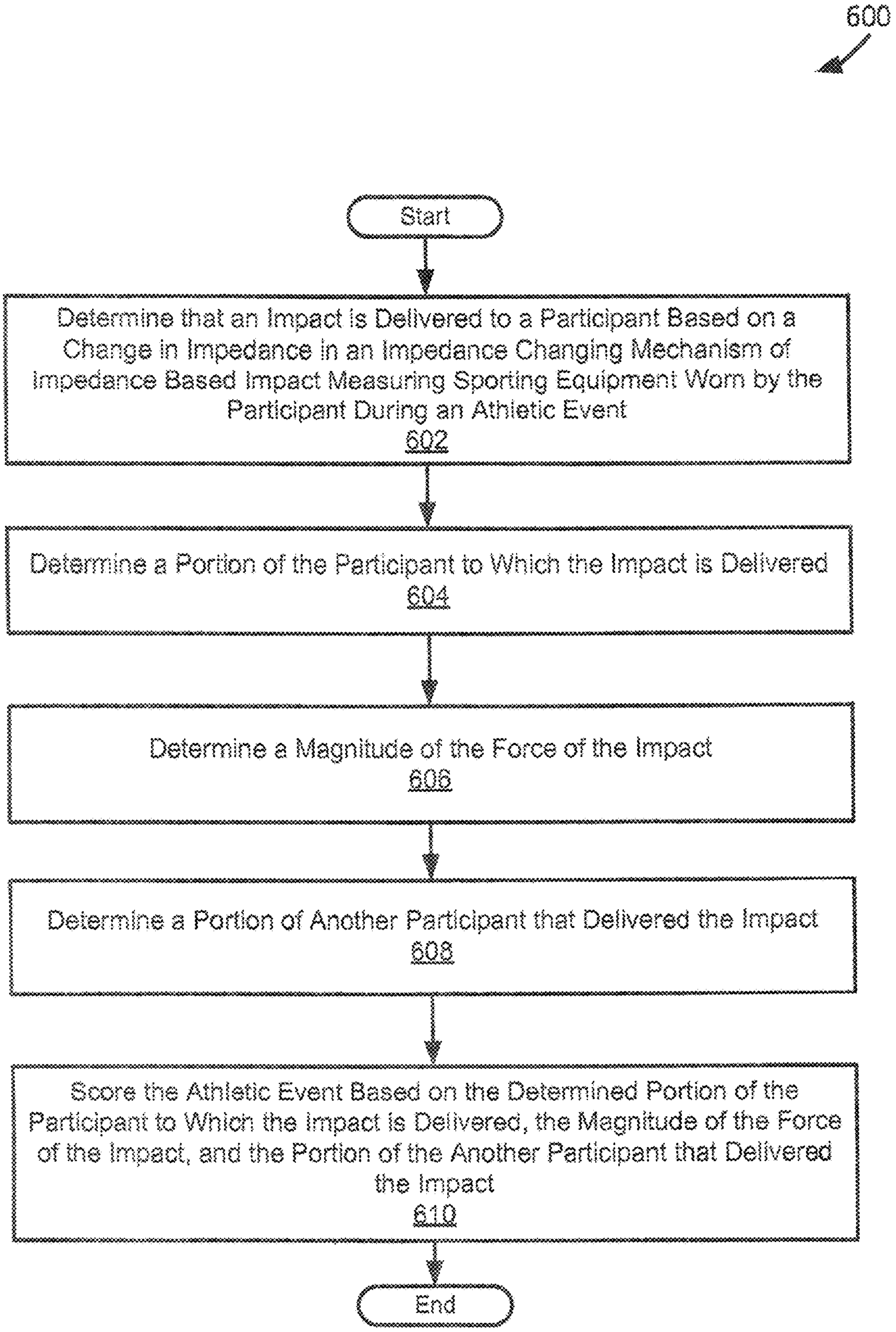
FIG. 6 depicts a flowchart of an example of a method for scoring an athletic event based on an impact delivered to a second participant determined by changes in impedance in an impedance changing mechanism.

FIG. 6 depicts a flowchart 600 of an example of a method for scoring an athletic event based on an impact delivered to a second participant determined by changes in impedance in an impedance changing mechanism. The flowchart 600 begins at module 602, where it is determined that an impact is delivered by a first participant using impedance-based impact measuring sporting equipment to a second participant using (e.g. wearing) impedance-based impact measuring sporting equipment based on a change in impedance in impedance changing mechanisms of the impedance-based impact measuring sporting equipment. In the context of this paper, the impedance-based impact measuring sporting equipment can refer to the equipment used by either or both (or all, if more than 2). In specific examples provided in this paper, each of two participants uses a portion of the impedance-based impact measuring sporting equipment, but it is possible to score events for teams where at any given time, a first participant from one team scores on a second participant of the other team in accordance with the descriptions provided herein, and the sum (or other function) of the individual scores for each team can be determined by considering each discrete scoring event.

Impedance in an impedance changing mechanism can change as a first participant delivers an impact with a portion of their body that includes a conductive material. Conductive material of a portion of a body used by a first participant can be included as part of impact measuring sporting equipment. An impedance changing mechanism of the impact measuring sporting equipment worn by a first participant can be coils of a conductive material through which a current is passed as part of an impedance-based impact sensing mechanism. As a conductive material is moved towards and away from the impedance changing mechanism, current which produce counter forces against an original current are generated in the impedance changing mechanism, causing the impedance to change as the conductive material is moved towards and away from the impedance changing mechanism and an impact is delivered to a second participant.

The flowchart 600 continues to module 604 where a portion of the second participant to which the impact is delivered is determined. A portion of the second participant to which the impact is delivered can be determined based on impedance characteristics specific to the impedance changing mechanism positioned on the body of the second participant. For example, based on impedance characteristics specific to the impedance changing mechanism, it can be determined that the impact occurs in the chest of a second participant using impedance-based impact measuring sporting equipment based on the position of the impedance changing mechanism. Impedance changing mechanism data can specify portions of a second participant at which specific impedance changing mechanisms are positioned. As a result, using the impedance changing mechanism and an identification of a specific impedance changing mechanism determined based on impedance characteristics specific to the impedance changing mechanism, the portion of the body of the second participant at which the impact was delivered can be determined, e.g. the portion of the body of the second participant that the impedance changing mechanism that experiences a change in impedance as a result of the delivery of the impact is positioned. Depending upon implementation-specific or other considerations, the specific impedance changing mechanism on the second participant can be determined based on rates at which impedance in the impedance changing mechanisms changes. Further depending upon implementation-specific or other considerations, the specific impedance changing mechanism can be determined based on a native impedance of the specific changing mechanism that experiences a change in impedance as a result of the delivery of the impact.

The flowchart 600 continues to module 606, where a magnitude of the force of the impact is determined. A magnitude of a force of the impact can be determined based on the rate at which impedance changes in the impedance changing mechanisms as a result of the impact. In determining a magnitude of a force of the impact based on a rate at which impedance changes in the impedance changing mechanism, the magnitude of the force of the impact can be determined by comparing the rate at which the impedance changes in the impedance changing mechanism to impedance changing rate data for the impedance changing mechanism. Impedance changing rate data for the impedance changing mechanism of the impedance-based impact measuring sporting can be predetermine d and specify magnitudes of forces of impact corresponding to specific rates at which impedance changes in the impedance changing mechanism. The flowchart 600 continues to module 608, where a portion of the first participant that delivers the impact is determined. In determining a portion of the first participant that delivers the impact, impact delivery characteristics data of the impedance-based impact measuring sporting equipment used by the second participant can be used to determine the portion of the first participant that delivers the impact. Impact delivery characteristics data of the impedance-based impact measuring sporting equipment worn by the first participant can specify a rate at which impedance changes in impedance changing mechanisms as a result of conductive materials positioned at different position on the first participant being moved towards and away from the impedance changing mechanisms as an impact is delivered. Specifically, impedance delivery characteristics data are different for conductive materials of different sizes or materials that are positioned at different portions of the first participant, e.g. a foot or a hand of the user. Using a rate at which impedance changes in the impedance changing mechanism of the second participant to which the impact is delivered and impact delivery characteristics of the impedance-based impact measuring sporting equipment worn by the first participant, a portion of a body of the first participant that delivers the impact to the user can be determined. For example, based on the rate at which the impedance changes in an impedance changing mechanism and impact delivery characteristics, it can be determined that a foot of the first participant delivered the impact to the second participant.

The flowchart 600 continues to module 610, where the athletic event is scored based on the determined portion of the second participant to which the impact is delivered, the magnitude of the force of the impact delivered to the second participant, and the portion of the first participant that delivered the impact. Additionally, the athletic event can be scored using impact scoring data for the athletic event. Impact scoring data for the athletic event can specify how to score, e.g. a number of points to award the first participant, based on where the impact is delivered, the magnitude of the force of the impact, and the portion of the first participant that delivers the impact.

Figure 7:
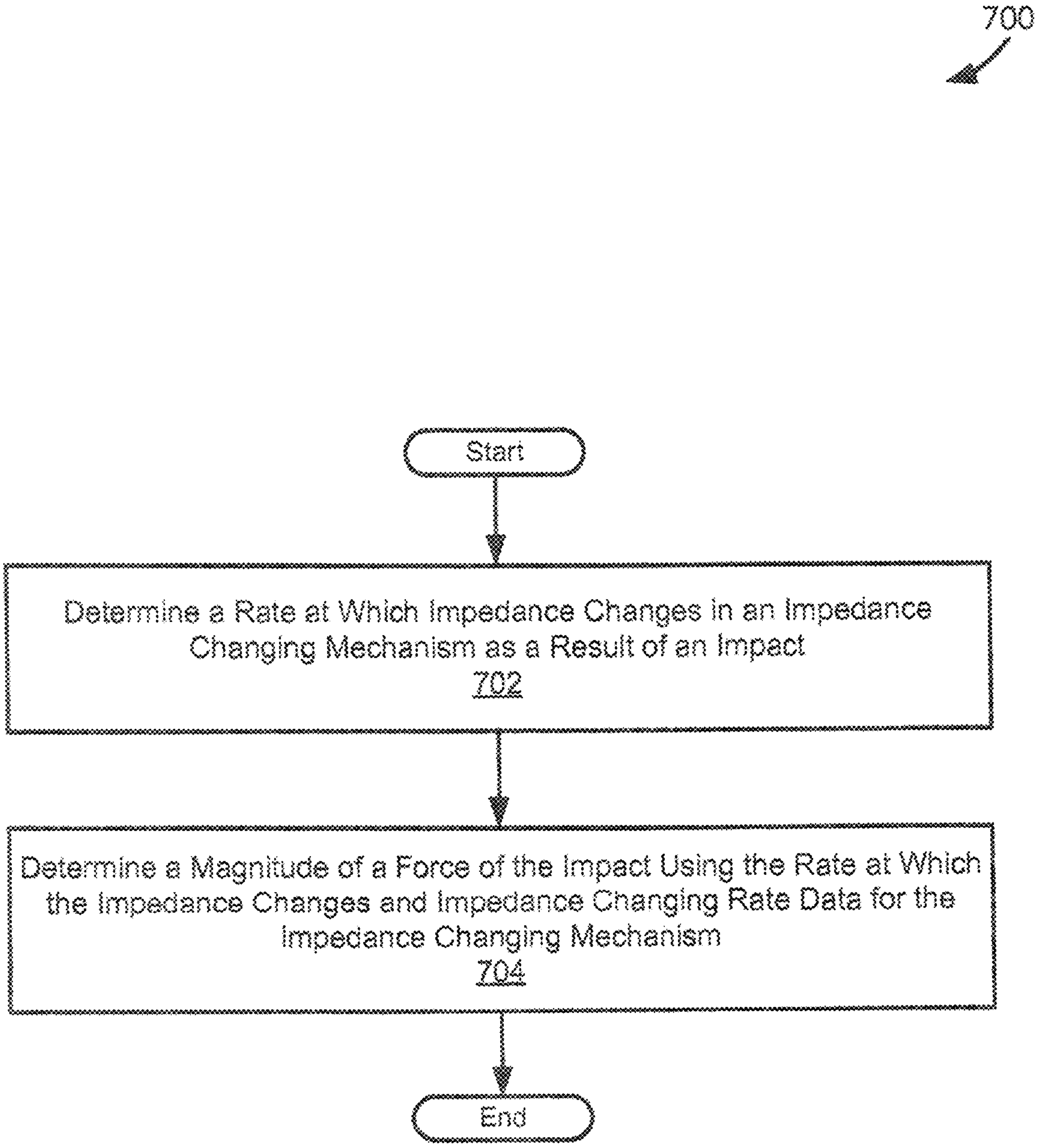
FIG. 7 depicts a flowchart of an example of a method for determining a magnitude of a force of an impact using impedance-based impact measuring sporting equipment.

FIG. 7 depicts a flowchart 700 of an example of a method for determining a magnitude of a force of an impact using impedance-based impact measuring sporting equipment. The flowchart 700 begins at module 702, where a rate at which impedance changes in an impedance changing mechanism as a result of an impact is determined. As the impact occurs a conductive material is moved towards and away from an impedance-based input sensing mechanism that causes impedance in an impedance changing mechanism included in the impedance-based input sensing mechanism to change. Depending upon implementation-specific or other considerations a rate at which an impedance changes can be determined from a signal that is received from a digital converter that is either part of or coupled to an impedance-based impact sensing mechanism that includes an impedance changing mechanism. The flowchart 700 continues to module 704 where a magnitude of a force of impact is determined based on the rate at which the impedance changes in an impedance changing mechanism and impedance changing rate data for the impedance changing mechanism. Impedance changing rate data can include specific forces that correspond to specific impedance rate changes for the specific impedance changing mechanism. As a result, based on a rate at which impedance changes in the impedance changing mechanism, as determined at module 702, a magnitude of a force of the impact can be determined.

Figure 8:
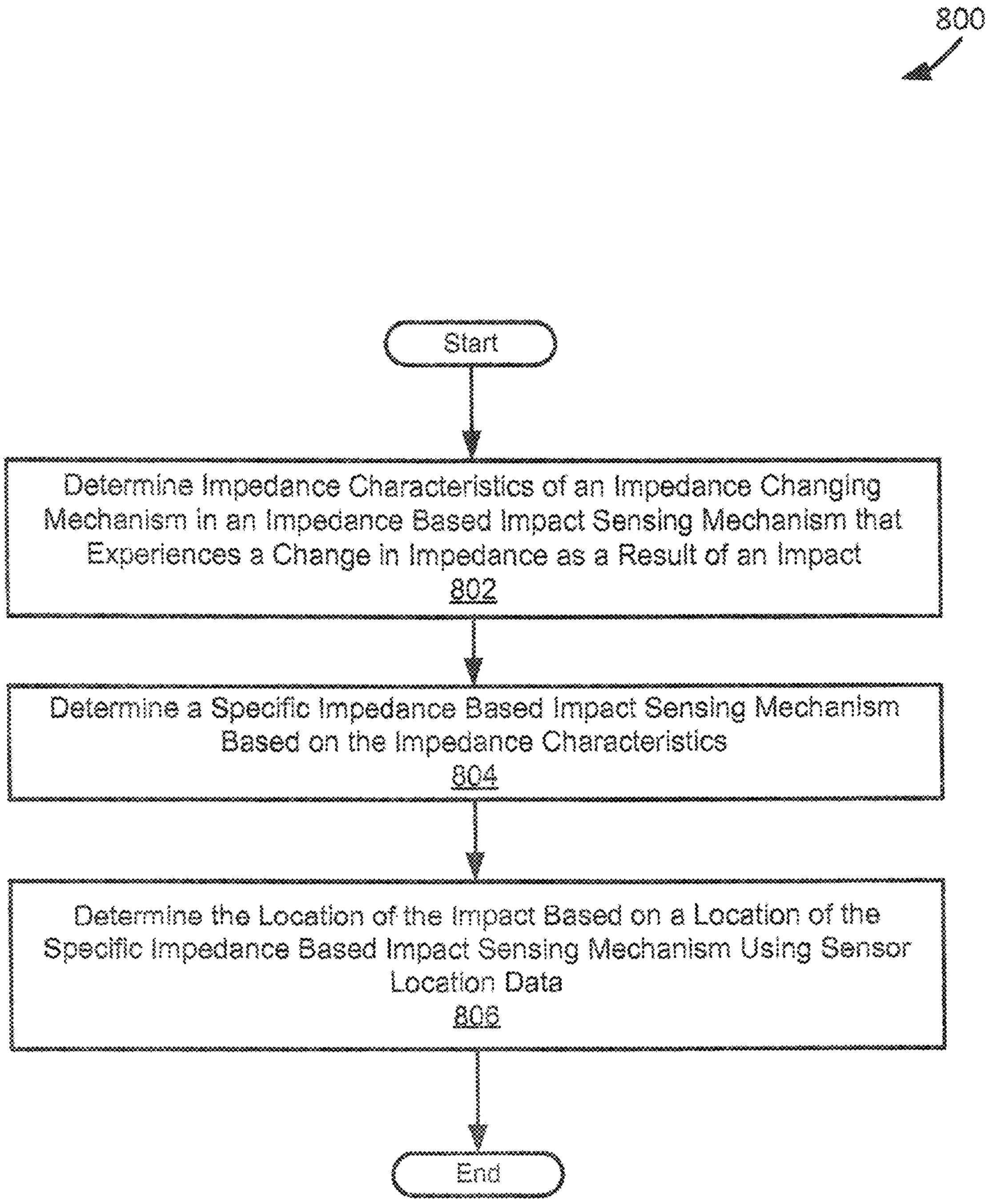
FIG. 8 depicts a flowchart of an example of a method for determining an impact location using impedance-based impact measuring sporting equipment.

FIG. 8 depicts a flowchart 800 of an example of a method for determining an impact location using impedance-based impact measuring sporting equipment. The flowchart 800 begins at module 802, where impedance characteristics of an impedance changing mechanism in an impedance-based impact sensing mechanism are determined. An impedance changing mechanism can have a change in impedance as a conductive material is moved towards and away from the impedance changing mechanism as an impact is delivered. Impedance characteristics of an impedance changing mechanism can include a native impedance of the impedance changing mechanism, a rate at which impedance changes in the impedance changing mechanism, or an impedance value that an impedance in the impedance changing mechanism changes to as a result of a conductive material moved towards and away from the impedance changing mechanism. The flowchart 800 continues to module 804, where a specific impedance-based impact sensing mechanism is determined based on the impedance characteristics determined at module 804. A specific impedance-based impact sensing mechanism can be determined from impedance characteristics data. Impedance characteristics data can include impedance characteristics of impedance changing mechanisms and identification of the impedance-based impact sensing mechanisms that include the impedance changing mechanisms. As a result, the determined impedance characteristics can be matched with an impedance changing mechanism in impedance characteristics data to determine a specific impedance-based impact sensing mechanism.

The flowchart 800 continues to module 806, where an impact location is determined based on a location of the specific impedance sensing mechanism is determined using sensor location data. Sensor location data can indicate the positions on a participant that impedance-based impact sensing mechanisms are positioned. As a result, in determining a specific impedance sensing mechanism that experiences a change in impedance as a result of an impact to a participant, the location of the specific impedance sensing mechanism can be determined. The location of the specific impedance sensing mechanism can correspond to a location of the impact or a location that is proximal to the location of the impact.

Figure 9:
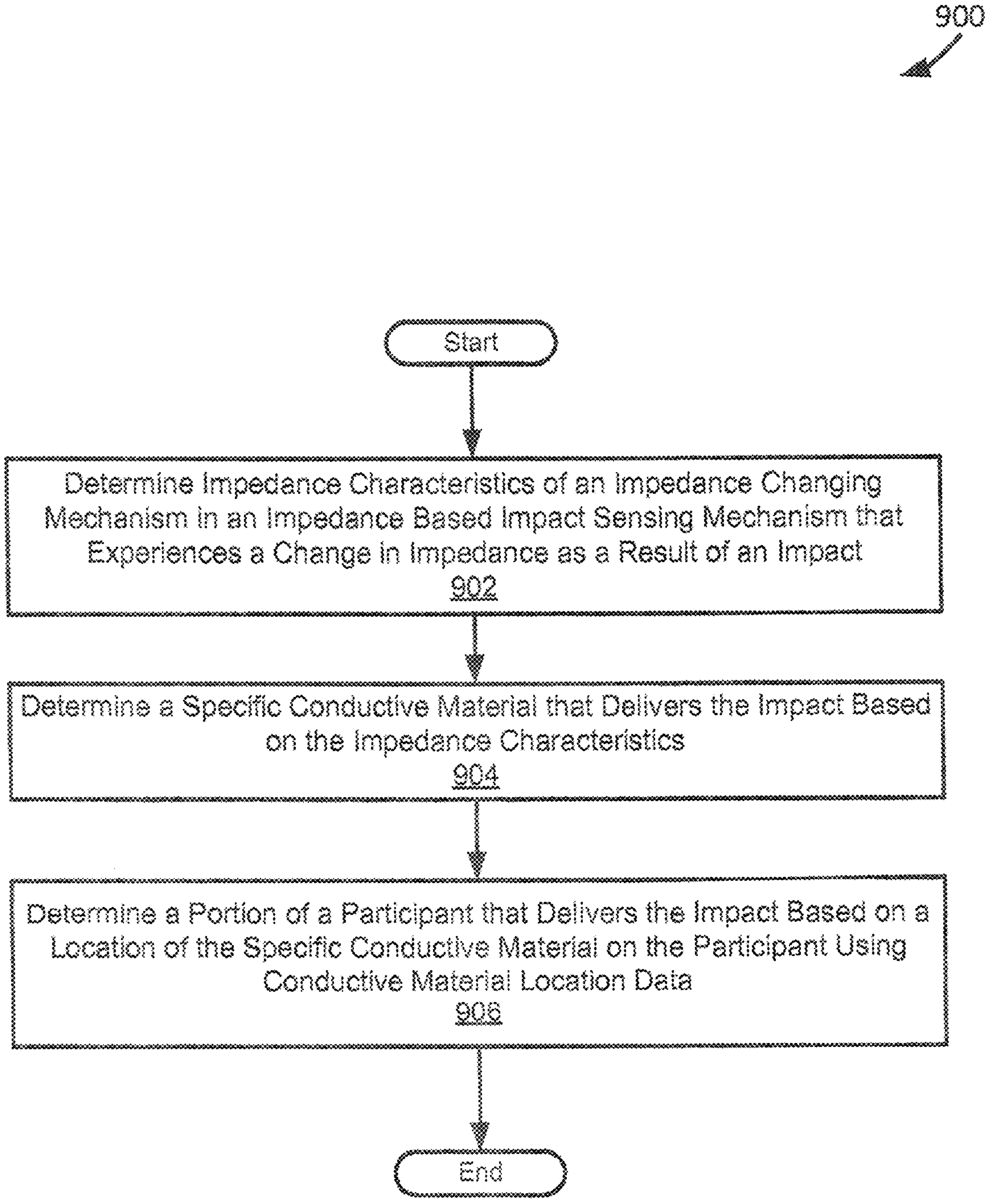
FIG. 9 depicts a flowchart of an example of a method for determining a portion of a participant that delivers an impact using impedance-based impact measuring sporting equipment.

FIG. 9 depicts a flowchart 900 of an example of a method for determining a portion of a participant that delivers an impact using impedance-based impact measuring sporting equipment. The flowchart 900 begins at module 902, where impedance characteristics of an impedance changing mechanism in an impedance-based impact sensing mechanism are determined. An impedance changing mechanism can have a change in impedance as a conductive material is moved towards and away from the impedance changing mechanism as an impact is delivered. Impedance characteristics of an impedance changing mechanism can include a native impedance of the impedance changing mechanism, a rate at which impedance changes in the impedance changing mechanism, or an impedance value that an impedance in the impedance changing mechanism changes to as a result of a conductive material moved towards and away from the impedance changing mechanism. The flowchart 900 continues to module 904, where a specific conductive material that delivers the impact is determined based on the impedance characteristics determined at module 902. A specific conductive material that delivers the impact can be determined based on impedance characteristics data. Impedance characteristics data can include specific conductive materials that cause impedance to change in impedance changing mechanisms at different rates. The flowchart 900 continues to module 906, where a portion of a participant that delivers the impact is determined based on a location of the specific conductive material, determined at module 904, on the participant. A location of the specific conduction material on a participant can be determined from conductive material location data. A determined location of the specific conduction material on a participant corresponds to a portion of the participant that delivers the impact.

Figure 10:
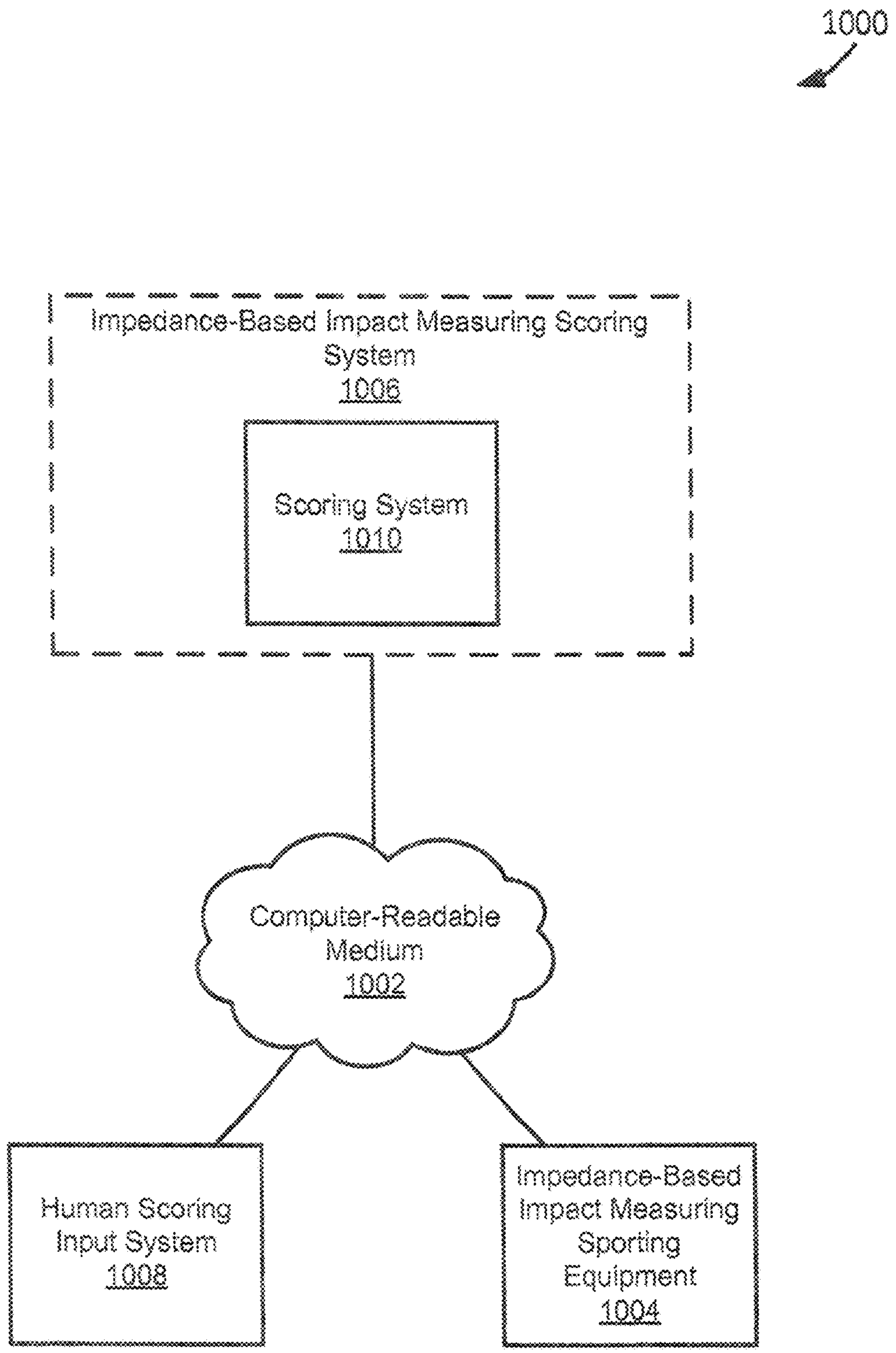
FIG. 10 depicts a diagram of an example of a system for scoring an athletic event using impedance-based impact measuring sporting equipment and human scoring input.

FIG. 10 depicts a diagram 1000 of an example of a system for scoring an athletic event using impedance-based impact measuring sporting equipment and human scoring input. The example system shown in FIG. 10 includes a computer-readable medium 1002, an impedance-based impact measuring sporting equipment 1004, an impedance-based impact measuring scoring system 1000, and a human scoring input system 1008. In the example system shown in FIG. 10, the impedance-based impact measuring sporting equipment 1004, the impedance-based impact measuring scoring system 1006, and the human scoring input system 1008 are coupled to each other through the computer-readable medium 1002. In a specific implementation, the impedance-based impact measuring sporting equipment functions according to applicable devices for determining impacts based on impedance, such as the impedance-based impact measuring sporting equipment described in this paper. The impedance-based impact measuring sporting equipment 1004 can include sensors that are used to measure impacts during an athletic event. Depending upon implementation-specific or other considerations, sensors included as part of the impedance-based impact measuring sporting equipment 1004 can include an applicable combination of impedance based impact sensing mechanisms, gyroscopes, and/or inertial measurement units (hereinafter referred to as IMUs). Further depending upon implementation-specific or other considerations, sensors included as part of the impedance-based impact measuring sporting equipment 1004 can be arranged in a sensor matrix.

In another implementation, the impedance-based impact measuring scoring system 1006 functions according to an applicable system for scoring an athletic event using impedance-based impact measuring sporting equipment, such as the impedance-based impact measuring scoring systems described in this paper. Depending upon implementation-specific or other considerations, the impedance-based impact measuring scoring system 1006 can determine impacts and magnitudes of forces of impact based on feedback received from either or both impedance sensing mechanisms, gyroscopes, and/or IMUs. Further depending upon implementation-specific or other considerations, the impedance-based impact measuring scoring system 1006 can be configured to query and/or receive input from a human scoring an athletic event.

In still another embodiment, the human scoring input system 1008 functions to allow a human to input data used in scoring an athletic event. Depending upon implementation-specific or other considerations, a human can input data used in scoring an athletic event using the human scoring input system 1008 after receiving a query for input from the impedance-based impact measuring scoring system 1006. A human can input data used to score an athletic event through the human scoring input system 1008 depending upon the types of movements or impacts that are delivered during an athletic event. For example, if a move is executed that requires or has been determined to be only scored by a human, then a human can input data used in scoring the move using the human scoring input system 1008. In the example system shown in FIG. 10, the impedance-based impact measuring scoring system 1006 includes a scoring system 1010. The scoring system 1010 can function according to an applicable system for scoring an athletic event using impedance-based impact measuring sporting equipment, such as the scoring systems described in this paper. The scoring system 1010 can function to score an athletic event based on portions of a first participant that deliver an impact to a second participant, a location where the impact is delivered onto a second participant, and a magnitude of a force of the delivered impact. Depending upon implementation-specific or other considerations, the scoring system 1010 can score an athletic event based on input received from a human through the human scoring input system 1008. For example, if input received from a human indicates to award three points, then the scoring system 1010 can award three points.

FIG. 10 depicts a diagram 1000 of an example of impedance-based impact measuring sporting equipment. Depending upon implementation-specific or other considerations, the impedance-based impact measuring sporting equipment can include systems and designs detailed in U.S. Pat. No. 7,891,231. A metallic fiber cloth has been added to the target area on the second participant's protective garment (2). The inductive sensor coil embedded in the first participant's glove (1) allows the transmitter to detect contact with the metallic fiber cloth area, tagging the related impact as a punch technique. The impact signal may then be modified or given a unique set of criteria for qualification. Alternatively or in addition, the first participant's glove can be configured to enable determining whether the strike landed was a punch or, e.g. a palm strike using one or more inductive sensor coils. Alternatively or in addition, the first participant's footwear can be configured to enable determination of a kick. Alternatively or in addition, the foot ware can be configured to enable determining whether the strike landed was a push kick or e.g., a heel kick (or to differentiate between kicks with a primary impact surface on the top of the foot, the edge of the foot, or the like).

Figure 11:
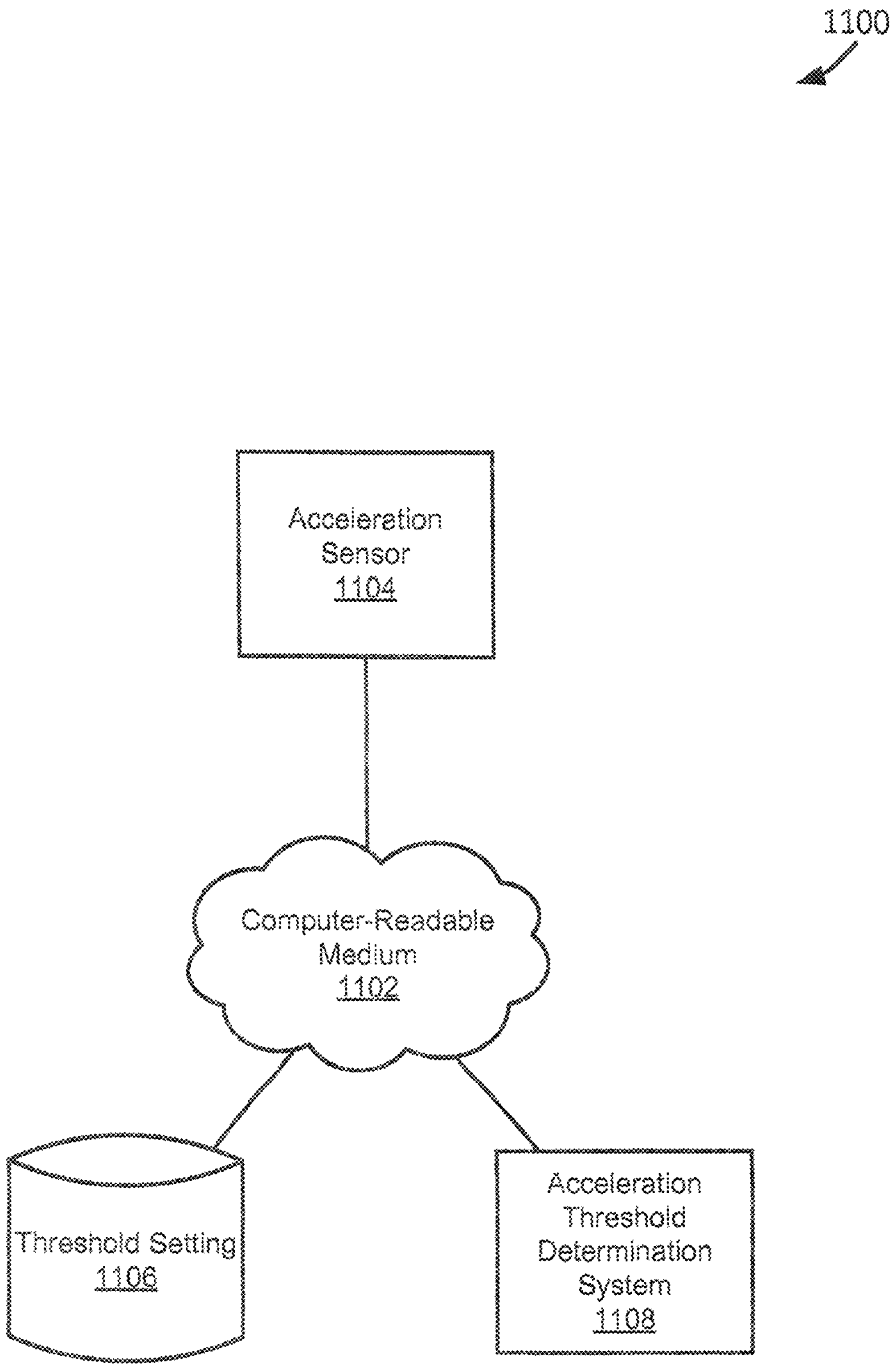
FIG. 11 depicts a diagram of an example of a system used to measure acceleration of a participant in an athletic event.

FIG. 11 depicts a diagram 1100 of an example of a system used to measure acceleration of a participant in an athletic event. Depending upon implementation-specific or other considerations, the example system shown in FIG. 11 can be included as part of an applicable device or system using in scoring an athletic event, such as the impedance-based impact measuring sporting equipment described in this paper, and/or the impedance-based impact measuring scoring systems described in this paper. The example system shown in FIG. 11 includes a computer-readable medium 1102, an acceleration sensor 1104, a threshold setting datastore 1106, and an acceleration threshold determination system 1108. In the example system shown in FIG. 11, the acceleration sensor 1104, the threshold setting datastore 1106, and the acceleration determination system 1108 are coupled to each other through the computer-readable medium 1102. In a further embodiment, the acceleration sensor 1104 functions according to an applicable sensor for measuring acceleration of a participant in an athletic event. The acceleration sensor 1104 can include one or a plurality of acceleration sensors that work together. Depending upon implementation-specific or other considerations, the acceleration sensor 1104 can include one of or an applicable combination of accelerometers, and/or IMUs. The acceleration sensor 1104 can function to measure acceleration of a participant in an athletic event as impacts are delivered to the participant.

In yet another embodiment, the threshold setting datastore 1106 functions to store threshold accelerations for an acceleration sensor 1104. Threshold accelerations stored in the threshold setting datastore 1106 can be specific to acceleration sensors, whereby different acceleration sensors have different acceleration thresholds. Depending upon implementation-specific or other considerations, acceleration sensors can have different acceleration thresholds based on corresponding positions of the acceleration sensors on a participant. Threshold accelerations can be used to differentiate between different moves performed during an athletic event and different impacts that are received during an athletic event. For example, if an acceleration, as determined by an acceleration sensor, exceeds a first acceleration threshold, then it can be determined that a specific move was executed or an impact was received that corresponds to the first acceleration threshold during an athletic event.

In a further embodiment, the acceleration threshold determination system 108 functions to determine whether an acceleration sensed by an acceleration sensor on a participant of an athletic event exceeds an acceleration threshold for the acceleration sensor. If an acceleration is determined by the acceleration threshold determination system 1108 to exceed an acceleration threshold, then the acceleration threshold determination system 1108 can store the acceleration value of the acceleration determined to exceed the acceleration threshold. Depending upon implementation-specific or other considerations, the acceleration threshold determination system 1108 can send an acceleration value of an acceleration that is determined to exceed an acceleration threshold for an acceleration sensor to an applicable system for scoring an athletic event, such as the impedance-based impact measuring scoring systems described in this paper. An acceleration value sent by the acceleration threshold determination system 1108 can be used to score an athletic event by an applicable scoring system to which the acceleration value is sent. Further depending upon implementation-specific or other considerations, the acceleration threshold determination system 1108 can be configured to record all acceleration values of accelerations determined by an acceleration sensor, regardless of whether the accelerations surpass an acceleration threshold. Acceleration values recorded by acceleration threshold determination system 1108 can further be used to score an athletic event, e.g. in the event of a tie in the athletic event.

Figure 12:
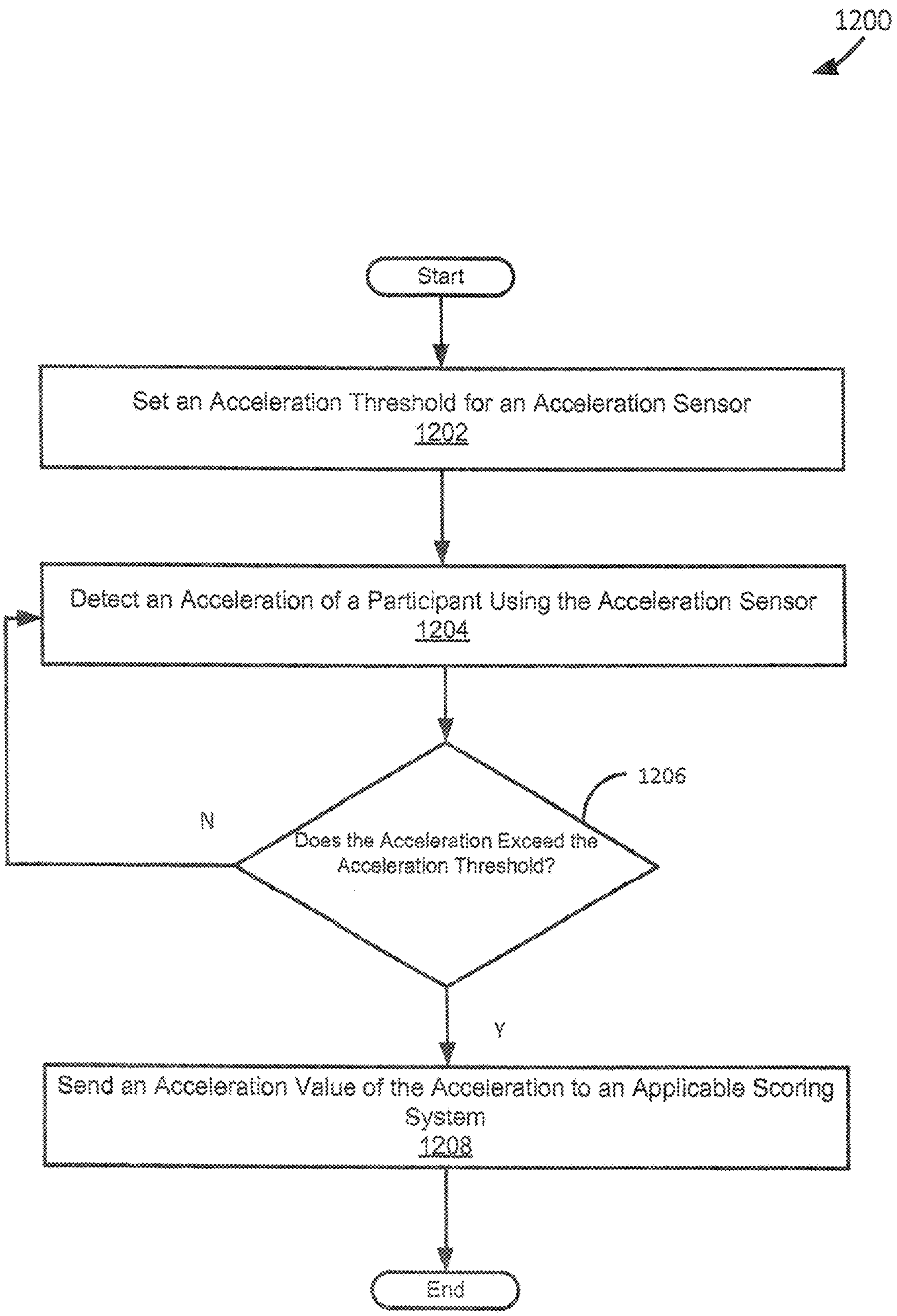
FIG. 12 depicts a flowchart of an example of a method for scoring an athletic event using acceleration thresholds for an acceleration sensor.

FIG. 12 depicts a flowchart 1200 of an example of a method for scoring an athletic event using acceleration thresholds for an acceleration sensor. The flowchart 1200 begins at module 1202, where an acceleration threshold is set for an acceleration sensor. An acceleration threshold can be an acceleration value that corresponds to a particular move that is performed during an athletic event or an impact that is delivered as a result of performance of the particular move during the athletic event. An acceleration threshold can be uniquely associated with a particular acceleration sensor. Depending upon implementation-specific or other considerations, a particular acceleration sensor can have multiple acceleration thresholds associated with the particular acceleration sensor. The flowchart 1200 continues to module 1204 where an acceleration of a participant is detected using the acceleration sensor. An acceleration of a participant detected by the acceleration sensor can be a result of another participant performing a particular move or delivering an impact during an athletic event. The flowchart 1200 continues to decision point 1206, where it is determined whether the acceleration, detected at module 1204 by the acceleration sensor, exceeds an acceleration threshold for the acceleration sensor. If it is determined at decision point 1206 that the acceleration does not exceed the acceleration threshold, then the flowchart 1200 continues back to module 1204 where an acceleration of a participant is detected using the acceleration sensor. Optionally, an acceleration value of an acceleration that does not exceed an acceleration value of the acceleration sensor can be recorded and later used to score an athletic event, e.g. in the event of a tie break.

If it is determined at decision point 1206, that the acceleration exceeds the acceleration threshold, then the flowchart continues to module 1208. At module 1208, the flowchart 1200 includes sending an acceleration value of the acceleration to an applicable system for scoring an athletic event, such as the impedance-based impact measuring scoring systems described in this paper. Depending upon implementation-specific or other considerations an acceleration value of the acceleration sent at module 1208 can be used to determine either or both a move that is performed during an athletic event and a magnitude of a force of a delivered impact, that are thereby used to score the athletic event.

Figure 13A:
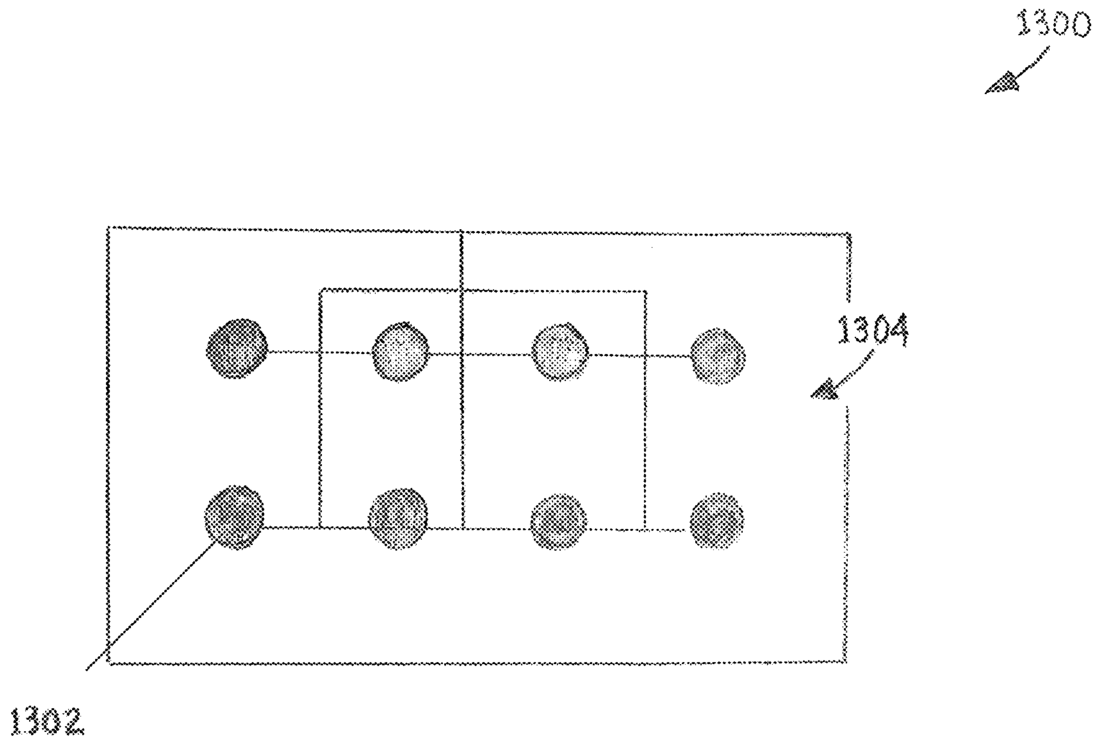
FIG. 13A-C depict diagrams of examples of a sensor matrix.

FIG. 13A depicts a diagram 1300 of an example of a sensor matrix. The sensor matrix includes a plurality of sensors 1302 arranged in an array 1304 and configured to detect impact to a participant wearing the sensor matrix. The sensors 1302 can include an applicable combination of impedance based impact sensing mechanisms, gyroscopes, and/or IMUs, including accelerometers. In including the sensors 1302 in an array 1304, a position of a sensor that detects an impact can be determined by an applicable system for determining a location at which an impact is delivered, such as the impact location determination systems described in this paper. A position of a sensor that detects an impact can be determined by vector analysis and/or quantifying the magnitude of forces of an impact as detected by nearby sensors to a central sensor that detects a highest magnitude of force of the sensors 1302 in the array 1304 as a result of an impact.

Figure 13B:
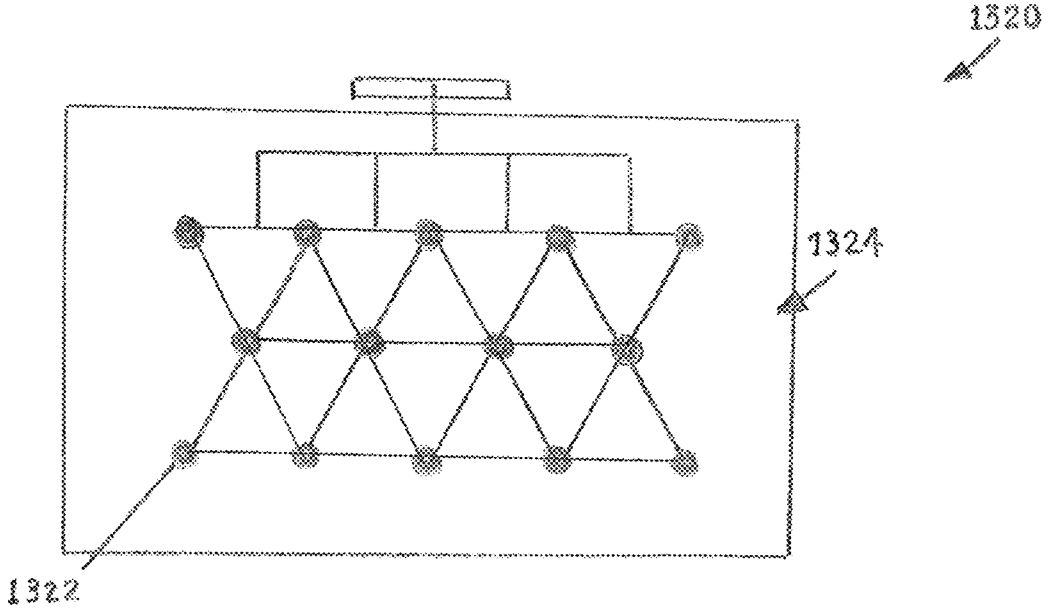

FIG. 13B depicts a diagram 1320 of another example of a sensor matrix. The sensor matrix includes a plurality of sensors 1322 arranged in a repeated triangular pattern 1324. The sensors 1322 can include an applicable combination of impedance based impact sensing mechanisms, gyroscopes, and/or IMUs, including accelerometers, and magnetometers. In including the sensors 1322 in a repeated triangular pattern 1324, a position of a sensor that detects an impact can be determined by an applicable system for determining a location at which an impact is delivered, such as the impact location determination systems described in this paper. A position of a sensor that detects an impact can be determine d by vector analysis and/or quantifying the magnitude of forces of an impact as detected by nearby sensors to a central sensor that detects a highest magnitude of force of the sensors 1324 in the repeated triangular pattern 1324, as a result of an impact.

Figure 13C:
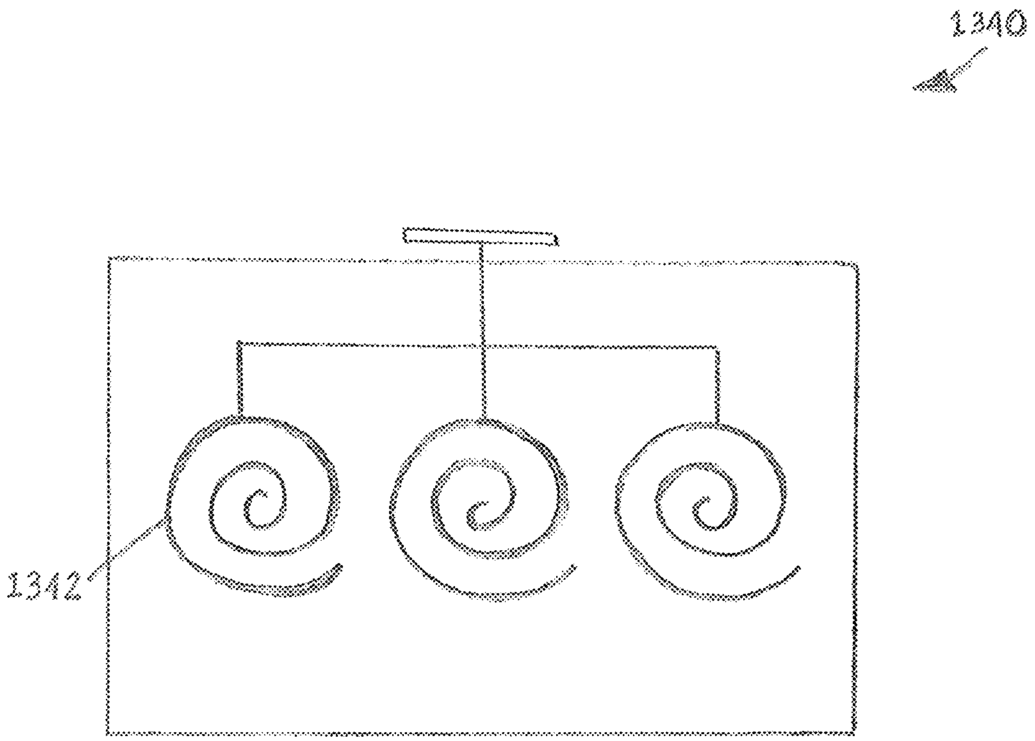

FIG. 13C depicts a diagram 1340 of another example of a sensor matrix. The sensor matrix includes a plurality of sensors 1342. The sensors 1342 shown in the example sensor matrix shown in FIG. 13C include multiple conductive material coils that serve as impedance changing mechanism or induction changing mechanism as conductive material or magnets are brought in proximity to the sensors 1342. Various systems using coils as sensing mechanisms are described in U.S. Pat. No. 7,891,231 B2, which is hereby incorporated by reference.

Figure 14:
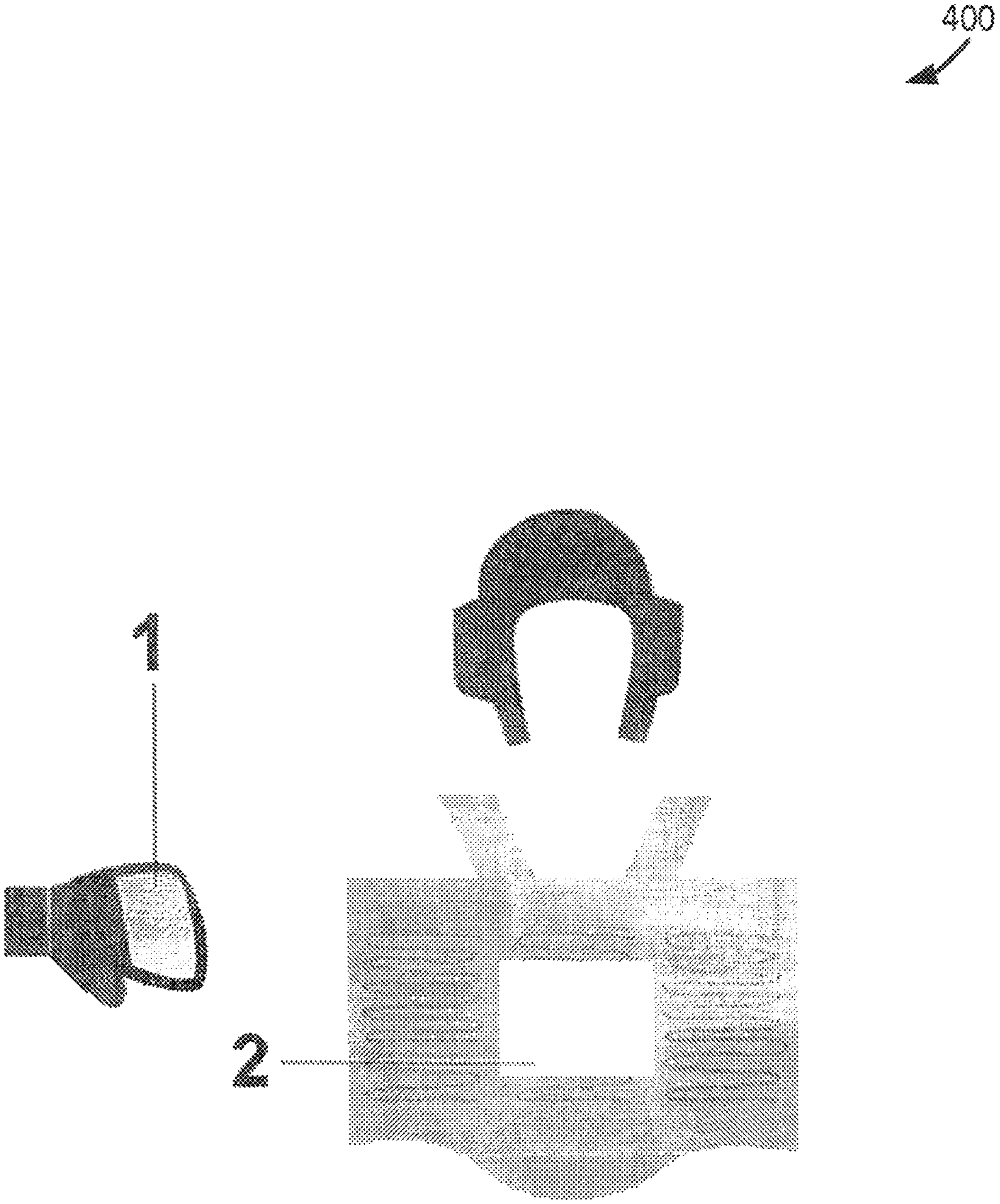
FIG. 14 depicts a diagram of another example of impedance-based impact measuring sporting equipment.

FIG. 14 depicts a diagram 1400 of another example of impedance-based impact measuring sporting equipment. The impedance-based impact measuring sporting equipment is applied to combative weapons sparring. The weapon's striking surface is layered with one or more impedance sensor coils (1). These coils terminate at the transmitter embedded in the weapon's handle (2), which maintains the radio link and performs any required data processing. The impedance-based impact measuring sporting equipment can also contain an accelerometer sensor to determine the severity of impact with the target area, e.g. a magnitude of a force of the impact.

Figure 15:
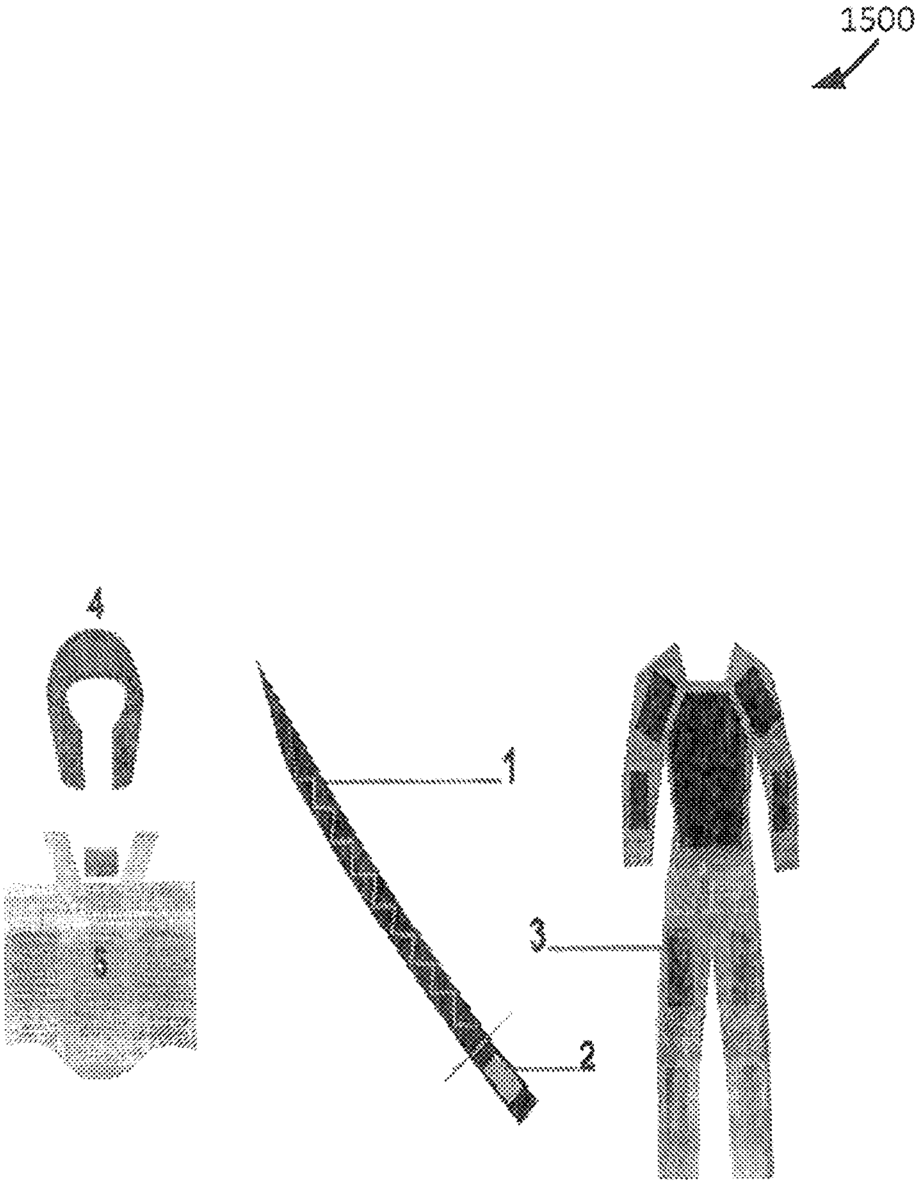
FIG. 15 depicts a diagram of another example impedance-based impact measuring sporting equipment.

FIG. 15 depicts a diagram 1500 of another example impedance-based impact measuring sporting equipment. In a specific implementation, a layer of metallic fiber cloth (3) is affixed to all valid target areas. To add an additional layer of discrimination, a magnetic proximity detector or piezoelectric impact sensor can be applied to secondary scoring areas or a helmet (4 and 5), worn underneath the protective armor.

Figure 16A:
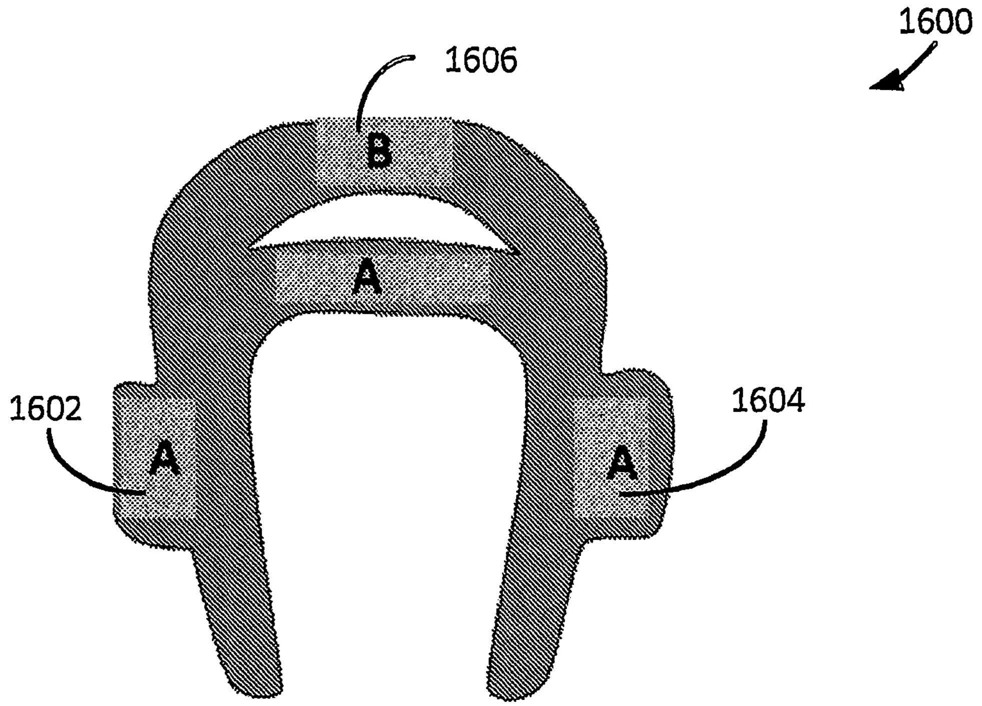
FIGS. 16A-B depict a diagram of an example of headgear included as part of impedance-based impact measuring sporting equipment.

FIG. 16A depicts a diagram 1600 of an example of headgear included as part of impedance-based impact measuring sporting equipment. The example headgear shown in FIG. 16A includes panels 1602 and 1604 filled with synthetic elastomeric polymer gel are positioned for optimal head protection. The example headgear shown in FIG. 16A also includes a pocket 1606 formed in the top of the headgear. The pocket 1606 can house specific sensor modules, such as an IMU, a 3-axis gyroscope and/or an acquisition/communications processor. Depending upon implementation-specific or other considerations, including a 3-axis gyroscope in the pocket 1606 allows the headgear to detect rotational movement, automatically scoring the technical difficulty bonus point for spinning kicks during sport Taekwondo matches.

Figure 16B:
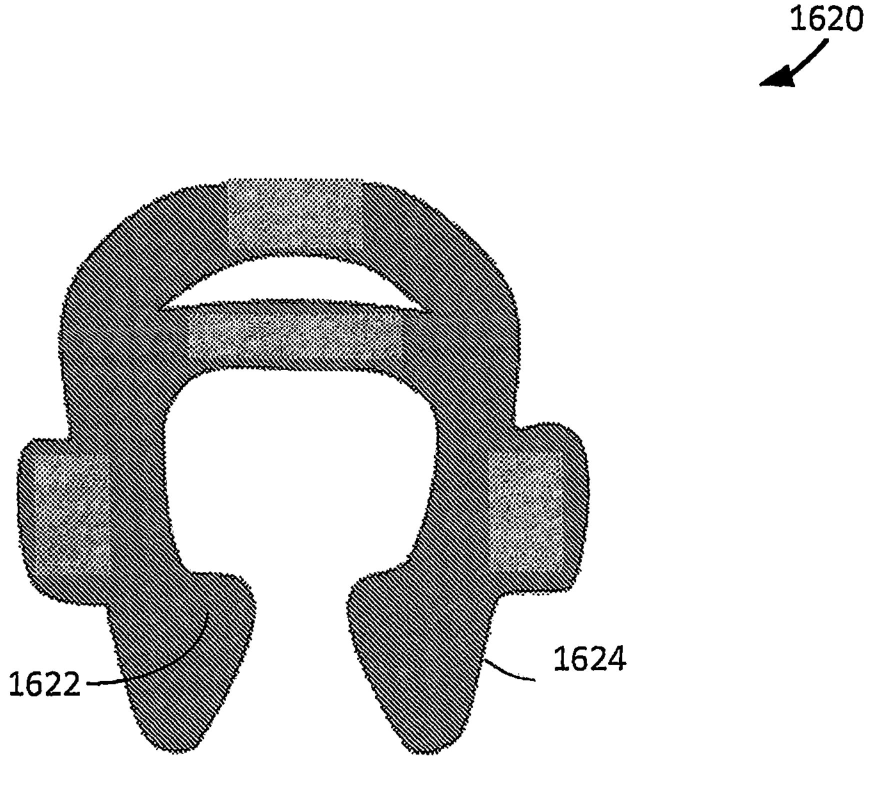

FIG. 16B depicts a diagram 1620 of another example of headgear included as part of impedance-based impact measuring sporting equipment. The example headgear shown in FIG. 16B can include the panels and pocket and corresponding sensor module as the example headgear shown in FIG. 16A. The example headgear shown in FIG. 16B includes extensions 1622 and 1624. The extensions 1622 and 1624 can be configured to extend across the neck or cheeks of a participant to protect the participant user from injury to the sides of the face. Depending upon implementation-specific or other considerations, the extensions 1622 and 162 can be used to mount additional sensors on a participant for use in scoring an athletic event.

Figure 17A:
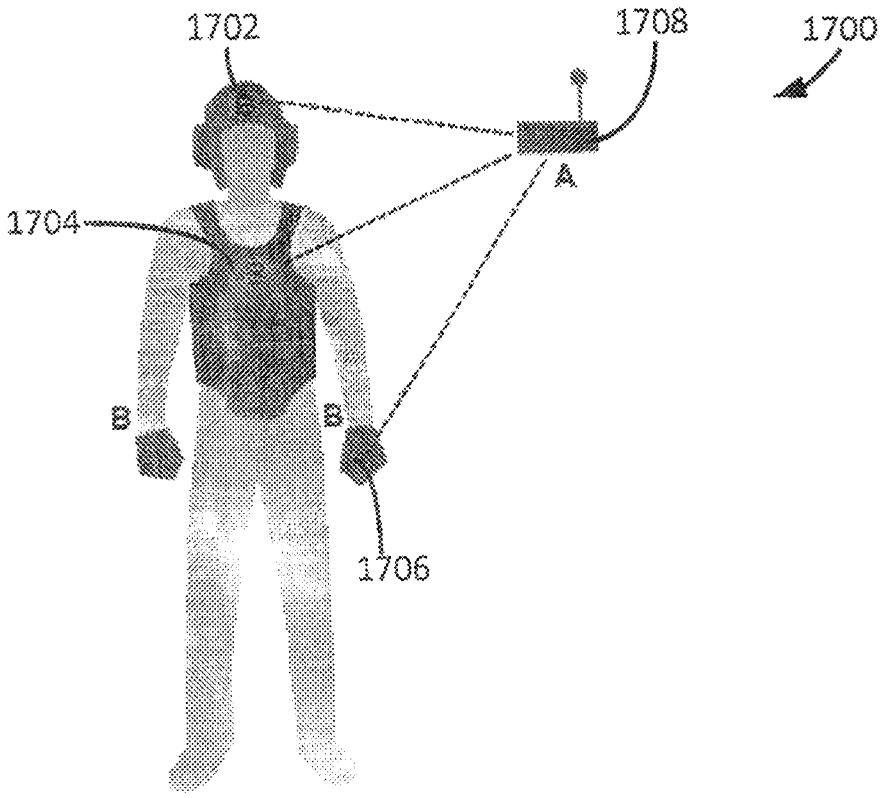
FIGS. 17A-B depict diagrams of examples of a system for scoring an athletic event wirelessly using impedance-based impact measuring sporting equipment.

FIG. 17A depicts a diagram 1700 of an example of a system for scoring an athletic event wirelessly using impedance-based impact measuring sporting equipment. The example system shown in FIG. 17A includes a plurality of sensor transmitters 1702, 1704, and 1706, on impedance-based impact measuring sporting equipment that are wirelessly coupled to a receiver 1708. Each of the plurality of sensor transmitters 1702, 1704, and 1706 are coupled to at least one sensor and function to transmit data from a sensor to the receiver 1708. Data transmitted by the sensor transmitters 1702, 1704, and 1706 to the receiver 1708 can be used to score an athletic event.

Figure 17B:
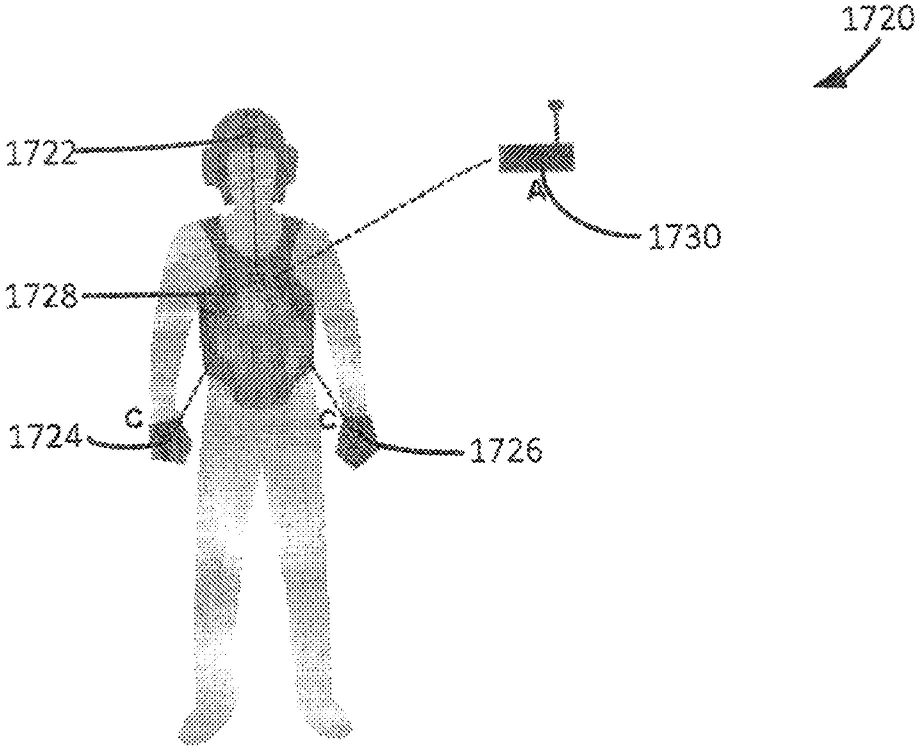

FIG. 17B depicts a diagram 1720 of another example of a system for scoring an athletic event wirelessly using impedance-based impact measuring sporting equipment. The system shown in FIG. 17B includes a plurality of sensors 1722, 1724, and 1726 coupled to an aggregator 1728. The aggregator 1728 can receive data from the sensors 1722, 1724, and 1726 based on impacts and movements detected by the sensors 1722, 1724, and 1726. Depending upon implementation-specific or other considerations, the sensors 1722, 1724, and 1726 can send data to the aggregator 1728 wirelessly, e.g. through an applicable low energy wireless connection. The aggregator 1728 is wirelessly coupled to a receiver 1730 and can function to wirelessly send data received from the plurality of sensors 1722, 1724, and 1726 to the receiver 1730. Data received by the receiver can be used in scoring an athletic event.

Figure 21:
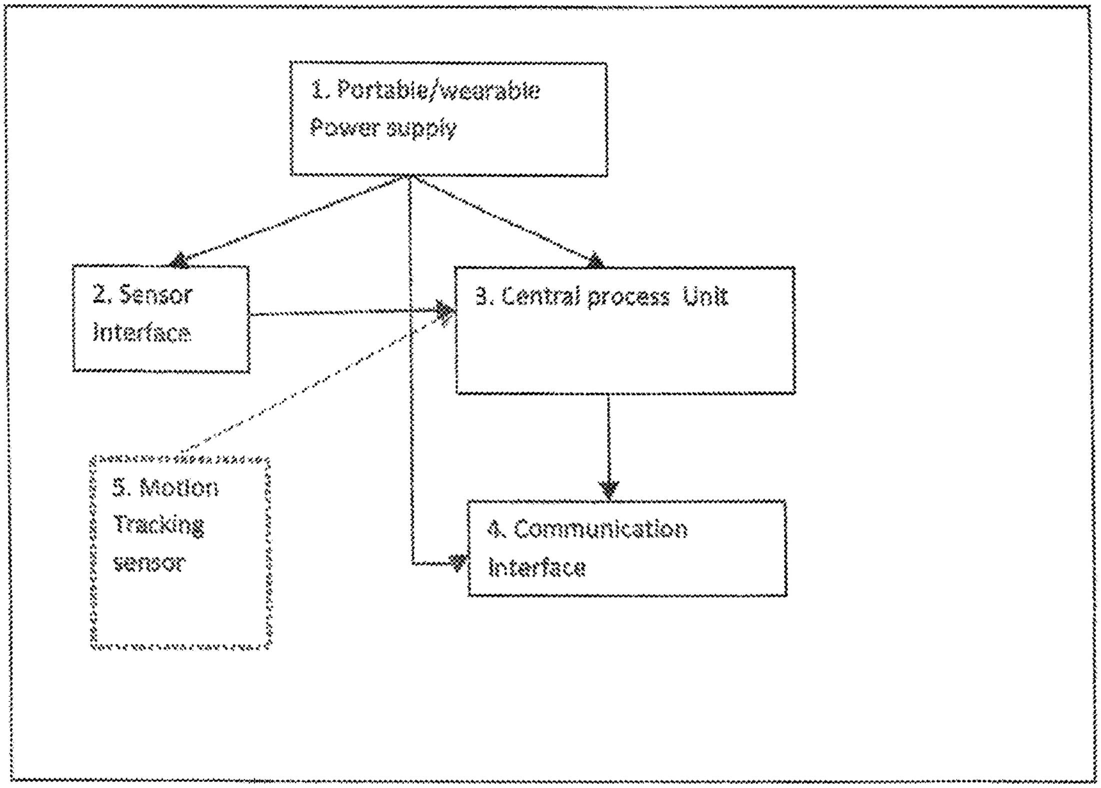
FIG. 21 shows the electronics that make up the sensor.

In an embodiment of the invention a nine-axis IMU in the form of a micro-electro-mechanical system (MEMS) that is with an electronic protector and scoring system. FIG. 21(4) details a typical nine-axis IMU, with the arrangement of sensors to detect both directional acceleration (accelerometer) and rotational movement (gyroscope) around three axes, change in orientation (magnetometer). In a typical application using nine axis sensors, three axis accelerometers are used to compute the orientation of the object (this is where the sensor is mounted) referenced to earth gravity, while three axis gyro is used to compute angular movement about the axis of sensitivity. The 3 axis magnetometer is used to measure heading orientation relative to the earth magnetic field. In the current application, only the three axis gyros will be used to compute the angular movement of the object since the gravity reference information is not important. 3 Axis magnetometer can also be used to measure angular movement relative to earth's magnetic field. Among the gyros, the axis parallel to the axis that represents the length of the body from head to toe is the most significant axis as shown later.

As can be seen in FIG. 18 and FIG. 19 the placement of the sensor may be positioned within the transmitter 2002 located in the chest protector 2001 (FIG. 18(1)) to measure the rotation of the player's torso or placed within the helmet transmitter 2003 in the helmet 2004 (FIG. 19(2)) to measure the rotation of the player's head. In both cases, one axis is oriented such that the axis is in alignment with the athlete's body from top to bottom. In the illustration, if the Z axis is aligned with the athlete's body, any rotation of the torso relative to the z axis can be measured and the angular distance the body rotates can be calculated by integrating the angular speed over time. As the sporting event progresses, the nine-axis IMU (mainly 3 gyros or 3 magnetometers) will monitor the rotational movement of the athlete. When the athlete's body performs a continuous rotation greater than a specific amount (e.g. 100°), the transmitter will send a time stamped data packet to the judge console, indicating to the software that the athlete has performed a turning motion. A software or filter may be applied to the data stream to minimize the effects of noise, or remove algorithm data resulting from non-technique related movements.

In FIGS. 18 and 19 players wear a chest protector 2001 with embedded sensor suite 2002. The sensor suite 2002 contains sensor electronics 2003, the sensor electronics are the three axis magnetometer, the three axis accelerometer and three axis gyroscope, acquires data and transmits the processed data to a base station (not shown). In FIG. 18(1), Sensor electronics 2003 are connected to the sensor suite 2. Glove sensors 2006 and shoe/sock sensors are the optional sensors that can be added to the system to increase the accuracy of scoring. The invention can be implemented with a full suite of sensors instead of only the combination of the three axis accelerometer and three axis gyroscope. The sensors will be communicating wirelessly directly to the receiver. In another configuration, it can have a subset of three axis magnetometer, three axis accelerometer and three axis gyroscope. In this case, it will send data to a transmitter. The transmitter will act as an aggregator to collect and process data to send to the receiver. The implementation will be detailed out in the later sections.

Figure 20:
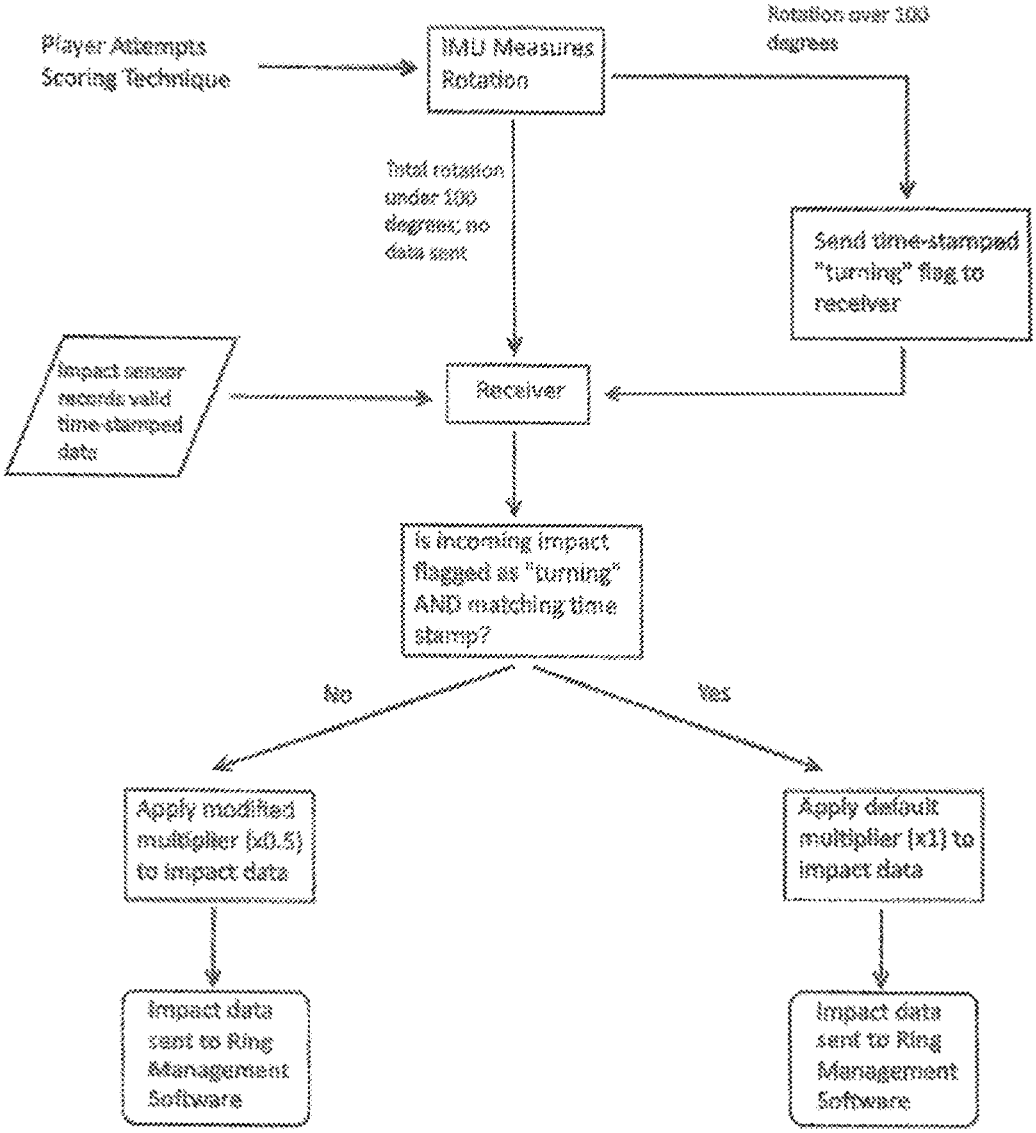
FIG. 20 shows an exemplary flowchart of the scoring process utilizing IMU.

FIG. 20 demonstrates an example of a scoring method that utilizes the nine-axis IMU for Taekwondo. During a match in progress, the inertial measurement unit will continuously monitor the athlete's rotation. When the athlete makes a quick rotation of at least 100 degrees in one direction, the IMU will alert the communications processor to send a "turning" flag to the referee's console ("receiver"). This data packet is time stamped at the moment of exceeding 100 degrees. When the body protector receives a valid impact event (proximity of striking surface to scoring area), the transmitter must make a check for the "turning" flag. If the "turning" data packet's timestamp matches the timestamp of the impact event, the transmitter sends the impact data directly to the ring management software to evaluate. If the "turning" flag is not present, or the time stamp does not match to within a specified time interval, the transmitter will modify the multiplier which effectively reduces the magnitude of the impact data. In this way, the impact data may be modified based on whether an athlete performs a turning kick, or a front leg technique (which typically does not involve rotation of the athlete's torso). The scoring adjustment is not limited to attenuation of the impact data. A variety of other scoring effects may be applied by classifying techniques by the amount of rotation. For example, additional points may be awarded for turning kicks or kicks that involve a full 360 degree rotation.

In FIG. 21, an expanded view of the sensor electronics 2003 is shown. A portable or wearable power supply could be rechargeable Lithium based batteries or off the shelf alkaline batteries. Sensor Interface is designed to connect to the impact and proximity sensor. The sensor hardware is designed to pre-process the analog impact and proximity sensor input from the chest protector (as an example) to feed into the central processor. The central processor Unit (CPU) is the intelligence that controls entire data acquisition, data processing and data transmission. The CPU converts the analog sensor signal to digital signal and performs signal processing mathematics to extract relevant information. It also executes signal detection decision algorithms based on user parameters. Once the data is acquired and processed, the CPU packetizes the information and sends it to the communication interface. The communication interface takes the packetized data and converts it to Radio Frequency signals that are defined by industry standards. There could be multiple standards, each providing features and functions that are preferred depending on the region of operation around the globe.

Figure 22:
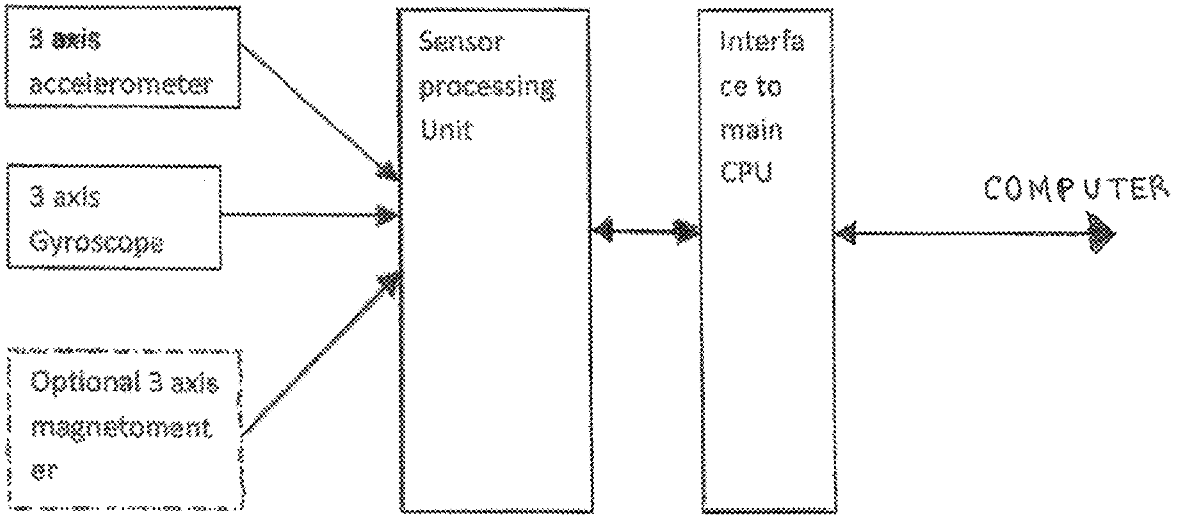
FIG. 22 shows the IMU sensor IC.

A motion tracking sensor is the additional sensor that provides further information in resolving ambiguities in competition. The sensors are an incremental addition to an existing hardware platform as shown in the figure. The existing CPU's software is modified to include the additional processing to extract useful information from the motion tracking sensor 10. The motion tracking sensor is derived from the traditional Inertial Measurement Unit (IMU). IMU is used mostly for navigation in aeronautics. The sensor technology was big and expensive. With the advent of Micro-machined Electro Mechanical Sensors (MEMS), the size is reduced to a single integrated circuit (IC) device, while the cost reduction has followed the drop in production cost due to high volume used in smart devices. The item is now a fully integrated single device that includes IMU sensor suites and a closely coupled co-processor that can perform math to extract motion tracking parameters such as orientation, angular and linear velocity. FIG. 22 illustrates the components within the IC. FIG. 23 shows the directions of the detectable accelerations and detectable angular rates.

As demonstrated in FIG. 6, by taking out the impact and proximity sensor, the hardware platform can be used in other motion tracking applications. The application could be anything that requires motion tracking. In some cases, communication could be implemented using cellular standards. In this case, the data can be monitored remotely from anywhere in the world to track the motion of the object that the sensor is attached to. With the addition of GPS, track position anywhere in the world.

Figure 24A:
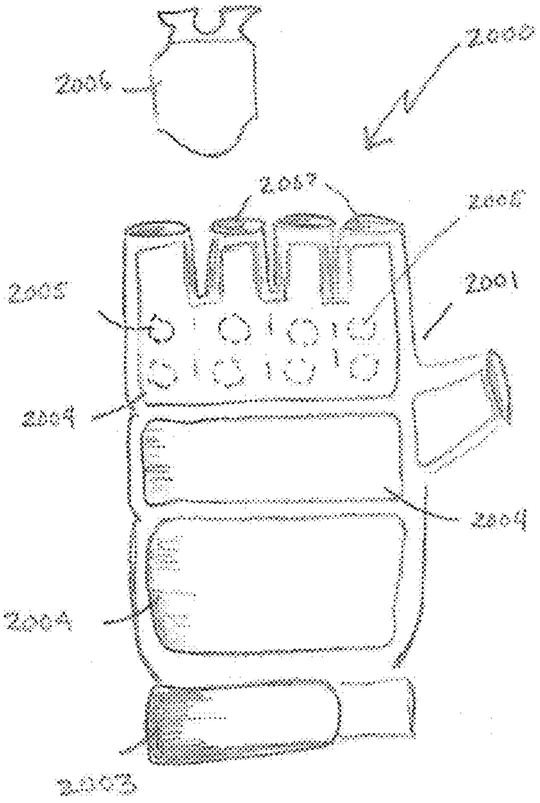
FIGS. 24A-B show the components of the gloves.
Figure 24B:
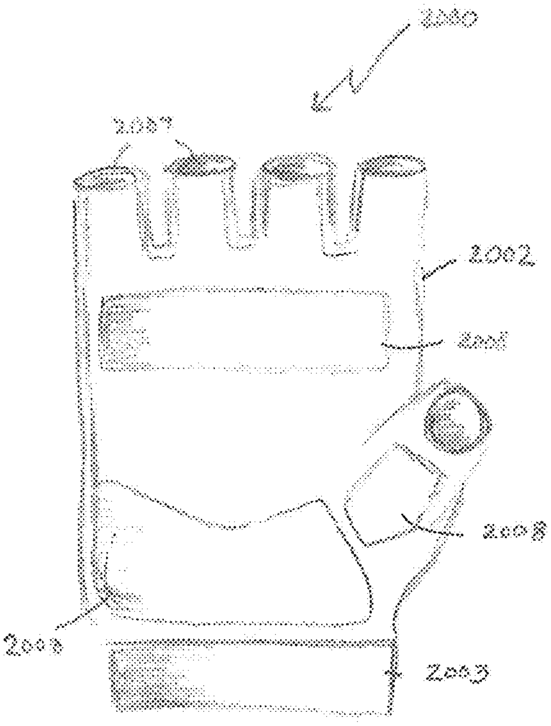

FIGS. 24A-B show the components of gloves. The gloves 2000 further comprise a topside 2001 as shown in FIG. 24A and an opposing palm side 2002 as shown in FIG. 24B, at least one adjustable strap 2003 to secure the glove to the user's wrist, padding 2004 inserted on the topside of the glove 2001, and the metal 2005 is embedded on the topside of the glove 2001 between the user's knuckles in order that only proper punches will be recorded by the detector 2006. In another embodiment, the gloves 2000 are fingerless and further comprises apertures 2007 for inserting the user's fingers, additional padding 2008 inserted on the opposing palm side 2002 of the gloves 2000 to allow for open handed blocking, and a portion for protecting the user's thumb, and the thumb portion being absent of metal.

Numerous modifications and variations of the present invention are possible in light of the above teachings. It is therefore to be understood that within the scope of the attendant claims attached hereto, this invention may be practiced otherwise than as specifically disclosed herein.

What is claimed is:

1. A motion tracking system for validating an athlete's movement technique to determine an accurate competitive scoring, said system with a nine-axis inertial measurement unit comprising:

a three axis accelerometer to measure the directional acceleration of an athlete's movement;

a three axis-gyroscope to measure the rotational motion of an athlete's movement;

a three axis-magnetometer to measure change in orientation and additional rotational motion of an athlete's movement; and at least one sensor attached to said three-axis accelerometer.

2. The system of claim 1 wherein at least one sensor is selected from the group consisting of an impact sensor, proximity sensor, magnetic proximity sensor, metal detector proximity sensor, three-axis magnetic compass and combinations thereof.

3. The system of claim 1 wherein the athlete's movement refers to a fighter's kicking and punching technique.

4. The system of claim 1 wherein said nine-axis inertial measurement unit is located in an article selected from a group consisting of an athlete's uniform, sporting equipment, protective equipment, clothing, wearable sports equipment, foot gear, gloves and combinations thereof.

5. The system of claim 1 wherein said sensor is located in an article selected from a group consisting of an athlete's uniform, sporting equipment, protective equipment, clothing, wearable sports equipment, foot gear, gloves and combinations thereof.

6. The system of claim 1 further comprising:

at least two conductive materials, each of said conductive materials coupled to a first and a second participant, each of said conductive materials configured to move when the first participant delivers an impact to the second participant using equipment;

at least one impedance-based impact sensing mechanism that detects a source of said impact comprising at least one impedance changing mechanism that changes impedance as each of said conductive material is moved towards and away from said impedance changing mechanism as the first participant delivers the impact;

at least one impact sensing mechanism using solely piezoelectric which mechanically detects the force of said impact creating electrical charges;

at least one impedance-based impact measuring scoring system determining the source of the impact that occurred based on a change in impedance electromagnetically in said impedance changing mechanism, determining the source of an impact prevents scoring impacts that are illegal; and at least one impedance changing rate determination engine configured to determine a rate at which the impedance changes in said impedance changing mechanism; and at least one impact force determination engine configured to determine a magnitude of a force of the impact based on the rate at which the impedance changes in said impedance changing mechanism and the impedance changing a rate data.

7. The system of claim 6 further comprises a sensor interface unit which is connected to said at least one sensor.

8. The system of claim 7 further comprises a central processor unit.

9. The system of claim 8 further comprises a communication interface unit.

10. The system of claim 9 wherein said central processor unit takes that data from said additional sensor interface unit to extract information and data regarding an athlete's movements.

11. The system of claim 10 wherein said central processor unit takes the data from said nine-axis inertial movement unit and combines it with said data from said sensor.

12. The system of claim 11 wherein said central processor unit then sends data regarding an athlete's movement to a base station, then said data is displayed on an electronic device.

13. The system of claim 12 wherein each of said three-axis sensors has a X, Y, and Z axis, one of the said Z axis aligns with an athlete's spine.

14. The system of claim 13 wherein an athlete's movement relative to the Z axis allows said three axis accelerometer to track the athlete's directional movement.

15. The system of claim 14 wherein an athlete's movement relative to the Z axis allows said three axis gyroscope to track the athlete's rotational movement.

16. A method for tracking athletic movement for accurate competitive scoring in martial arts, said method comprises:

assembling a nine-axis inertial measurement unit comprising a three axis magnetometer, a three-axis accelerometer, a three-axis gyroscope and a sensor interface unit;

attaching a sensor to said sensor interface unit;

measuring directional acceleration of an athlete's movement with said three-axis accelerometer;

measuring rotational motion of an athlete's movement with said three axis-gyroscope;

measuring rotational motion of an athlete's movement with said three axis-magnetometer; and recording movement data from said three axis magnetometer, said three-axis accelerometer, and said three-axis gyroscope with said sensor interface unit and then passing the movement data to a central processor unit for analysis.

17. The method of claim 16 further comprises the step of: attaching said nine-axis inertial measurement unit and said sensor in an article, said article is selected from the group consisting of an athlete's uniform, sporting equipment, protective equipment, clothing, wearable sports equipment, foot gear, gloves and combinations thereof.

18. The method of claim 17 further comprises the step of:

adding at least two conductive materials, each of said conductive materials coupled to a first and a second participant, each of said conductive materials configured to move when the first participant delivers an impact to the second participant using equipment;

adding at least one impedance-based impact sensing mechanism that detects a source of said impact comprising at least one impedance changing mechanism that changes impedance as each of said conductive material is moved towards and away from said impedance changing mechanism as the first participant delivers the impact;

adding at least one impact sensing mechanism using solely piezoelectric which mechanically detects the force of said impact creating electrical charges;

adding at least one impedance-based impact measuring scoring system determining the source of the impact that occurred based on a change in impedance electromagnetically in said impedance changing mechanism, determining the source of an impact prevents scoring impacts that are illegal; and adding at least one impedance changing rate determination engine configured to determine a rate at which the impedance changes in said impedance changing mechanism; and at least one impact force determination engine configured to determine a magnitude of a force of the impact based on the rate at which the impedance changes in said impedance changing mechanism and the impedance changing a rate data.

19. The method of claim 18 further comprising the step of:

adding a central processor unit and a communication interface unit;

allowing said central processor unit to take that data from said sensor interface unit to extract information and data regarding an athlete's movements;

allowing said central processor unit takes the data from said nine-axis inertial movement unit and combines it with said data from said sensor; and allowing said central processor unit to send data regarding an athlete's movement to a base station, then displaying said data on an electronic device.

20. The method of claim 19 further comprising the step of:

providing each of said three-axis sensors with a X, Y, and Z axis, and aligning one of the said Z axis with an athlete's spine;

allowing said three axis accelerometer to track the athlete's directional movement; and allowing said three axis gyroscope to track the athlete's rotational movement.

* * * * *